US010869851B1

(12) United States Patent
Ieronimakis et al.

(10) Patent No.: US 10,869,851 B1
(45) Date of Patent: Dec. 22, 2020

(54) TARGETING NUR77 FOR MITIGATING PERINATAL NEUROINFLAMMATION

(71) Applicant: The United States Government as represented by the Secretary of the Army, Fort Detrick, MD (US)

(72) Inventors: Nicholas M. Ieronimakis, Tacoma, WA (US); Andrew S. Thagard, Portsmouth, VA (US); Sarah M. Estrada, Lacey, WA (US); Peter Napolitano, Steilacoom, WA (US)

(73) Assignee: The United States Government as represented by the Secretary of the Army, Fort Detrick, MD (US)

(*) Notice: Subject to any disclaimer, the term of this patent is extended or adjusted under 35 U.S.C. 154(b) by 0 days.

(21) Appl. No.: 15/916,353

(22) Filed: Mar. 9, 2018

Related U.S. Application Data

(60) Provisional application No. 62/470,535, filed on Mar. 13, 2017, provisional application No. 62/622,585, filed on Jan. 26, 2018.

(51) Int. Cl.
*A61K 31/216* (2006.01)
*A61P 25/00* (2006.01)
*A61K 45/06* (2006.01)
*A61K 31/57* (2006.01)

(52) U.S. Cl.
CPC ............ *A61K 31/216* (2013.01); *A61K 45/06* (2013.01); *A61P 25/00* (2018.01); *A61K 31/57* (2013.01)

(58) Field of Classification Search
None
See application file for complete search history.

(56) References Cited

U.S. PATENT DOCUMENTS

2012/0183616 A1* 7/2012 Sprogoe

OTHER PUBLICATIONS

Zhan et al., "The orphan nuclear receptor Nur77 regulates LKB1 localization and activates AMPK", Nature Chemical Biology, vol. 8, pp. 897-904, Nov. 2012.*
Thagard et al., "Magnesium sulfate and betamethasone reduce NUR 77 expression in a preterm labor mouse model", Semanticscholar. org, downloaded on from "https://pdfs.semanticscholar.org/396c/3595222698db3b4fa8d41ab04815b2463306.pdf?_ga=2.58435055.472796938.1565731396-289092603.1565731396", 11 pages, Jun. 26, 2016.*
Köck et al., "Diabetes mellitus and the risk of preterm birth with regard to the risk of spontaneous preterm birth", The Journal of Maternal-Fetal & Neonatal Medicine, vol. 23(9), pp. 1004-1008, 2010; Summary document only.*
Doyle et al., "Antenatal Magnesium Sulfate and Neurologic Outcome in Preterm Infants", Obstetrics & Gynecology, vol. 113(6), pp. 1327-1333, Jun. 2009.*

* cited by examiner

*Primary Examiner* — Savitha M Rao
*Assistant Examiner* — Gregg Polansky
(74) *Attorney, Agent, or Firm* — Leigh Callander

(57) ABSTRACT

Compositions and methods of inhibiting Nur77 in a subject for treatment of perinatal neuroinflammation, preterm labor, or preterm birth are provided.

21 Claims, 12 Drawing Sheets

US 10,869,851 B1

TARGETING NUR77 FOR MITIGATING PERINATAL NEUROINFLAMMATION

RELATED APPLICATION INFORMATION

This application claims the benefit of U.S. 62/470,535, filed Mar. 13, 2017, and U.S. 62/622,585, filed Jan. 26, 2018, both of which are herein incorporated by reference in their entirety.

ACKNOWLEDGEMENT OF GOVERNMENT SUPPORT

This invention was made with government support from Madigan Army Medical Center, a subordinate organization of the United States Army Medical Command. The Government has certain rights in the invention.

BACKGROUND OF THE INVENTION

1. Field of the Invention

The present invention generally relates to methods and compositions for treating, inhibiting, or reducing diseases and disorders caused by perinatal neuroinflammation associated with Nur77 expression and signaling.

2. Description of the Related Art

Preterm labor and delivery remain a common problem worldwide despite considerable medical advances. The underlying mechanism of preterm labor is incompletely understood. However, intrauterine inflammation—whether from overt infection or a more insidious process—leading to cervical shortening and contractions may play a significant role [1]. The cost of preterm birth is dramatic, estimated at $26 billion annually [2]. The long-term implications are profound. Cerebral palsy (CP), a non-progressive mainly motor disorder, is one prominent example. Twelve percent of infants born prior to 27 weeks gestation develop CP [3]. The lifetime cost of caring for a single person with this condition was more than $900,000 in 2003 [4].

To date, interventions employed in the setting of overt or suspected preterm labor focus on one of two objectives: inhibiting the process and mitigating the complications [1], [2], [5]. The former includes tocolysis, progesterone therapy, and cerclage. Historically, the latter has consisted almost exclusively of corticosteroid therapy. Administration of steroids including betamethasone ("BMZ" or "BTMZ") and dexamethasone to a woman in preterm labor accelerates fetal lung maturation and reduces the incidence of intraventricular hemorrhage (IVH) and necrotizing enterocolitis (NEC) [6]. Steroids also have known anti-inflammatory properties [7].

More recently, magnesium sulfate ($MgSO_4$) for neuroprotection has been added to the clinician's standards of care for preterm labor. While observational studies dating back to the 1990s [8] suggest a possible neuroprotective benefit of $MgSO_4$, widespread clinical use was spurred by meta-analysis of several large randomized controlled trials [9] and a joint statement by the American College of Obstetricians and Gynecologists and the Society for Maternal Fetal Medicine. The precise mechanism by which $MgSO_4$ exerts a neuroprotective role remains unknown. $MgSO_4$ prevents a single case of cerebral palsy in 46 women in preterm labor [9]. Some research [10] suggests potential adverse neonatal effects from $MgSO_4$ administration. Maternal toxicity is an established serious complication. Understanding the mechanism of how $MgSO_4$ works may lead to the development of a more targeted therapy with fewer sequelae.

Therefore, a need exists for new treatment strategies for perinatal neuroinflammation associated preterm labor and preterm birth.

SUMMARY OF THE INVENTION

In some embodiments, the present invention provides a method of reducing or inhibiting expression of Nur77 or reducing or inhibiting Nur77 receptor signaling in a subject, which comprises administering to the subject an effective amount of one or more Nur77 antagonists. In some embodiments, the effective amount is a therapeutically effective amount. In some embodiments, the effective amount is a prophylactically effective amount. In some embodiments, the subject is in need thereof. In some embodiments, the subject is a fetus or a preterm baby. In some embodiments, the subject suffers from a Nur77 disease or disorder. In some embodiments, the Nur77 disease or disorder is perinatal neuroinflammation, a perinatal neurological injury, a vascular injury, a neurodevelopmental disability, or cerebral palsy. In some embodiments, the Nur77 disease or disorder is caused by preterm labor and/or preterm birth. In some embodiments, the one or more Nur77 antagonists is a nucleic acid molecule, a protein, a peptidomimetic, an antibody or an antigen-binding fragment (Fab) thereof, a ribozyme, or a small molecule. In some embodiments, the one or more Nur77 antagonists is ethyl 2-(2,3,4-trimethoxy-6-octanoylphenyl)acetate (TMPA) or a pharmaceutically acceptable salt thereof. In some embodiments, a prophylactically effective amount of the one or more Nur77 antagonists is administered to the subject. In some embodiments, a dose of the one or more Nur77 antagonists is administered before, during, and/or after preterm birth of the subject. In some embodiments, the subject is in need thereof. In some embodiments, the subject is a fetus or a premature baby. In some embodiments, the fetus is treated in utero by administering the one or more Nur77 antagonists to the mother. In some embodiments, the one or more Nur77 antagonists are administered to the subject in an amount of about 5 mg to about 500 mg per kg weight of the subject. In some embodiments, the one or more Nur77 antagonists are administered in the form of a pharmaceutical composition. In some embodiments, the method further includes administering to the subject magnesium sulfate and/or betamethasone. In some embodiments, the method further includes administering to the subject one or more supplementary agents. In some embodiments, the one or more supplementary agents is a corticosteroid, an immunosuppressant, an anti-inflammatory agent, an anti-ischemic agent, or a palliative agent.

In some embodiments, the present invention provides a method of preventing, treating, or inhibiting a Nur77 disease or disorder in a subject, which comprises reducing or inhibiting expression of Nur77 or reducing or inhibiting Nur77 receptor signaling in the subject by administering to the subject a therapeutically effective amount of one or more Nur77 antagonists. In some embodiments, the Nur77 disease or disorder is perinatal neuroinflammation, a perinatal neurological injury, a vascular injury, a neurodevelopmental disability, or cerebral palsy. In some embodiments, the Nur77 disease or disorder is caused by preterm labor and/or preterm birth. In some embodiments, the one or more Nur77 antagonists is a nucleic acid molecule, a protein, a peptidomimetic, an antibody or an antigen-binding fragment (Fab) thereof, a ribozyme, or a small molecule. In some embodiments, the one or more Nur77 antagonists is ethyl 2-(2,3,4-trimethoxy-6-octanoylphenyl)acetate (TMPA) or a pharmaceutically acceptable salt thereof. In some embodiments, a prophylactically effective amount of the one or more Nur77 antagonists is administered to the subject. In some embodiments, a dose of the one or more Nur77 antagonists is administered before, during, and/or after preterm birth of the subject. In some embodiments, the subject is in need thereof. In some embodiments, the subject is a fetus or a premature baby. In some embodiments, the fetus is treated in utero by administering the one or more Nur77 antagonists to the mother. In some embodiments, the one or more Nur77 antagonists are administered to the subject in an amount of about 5 mg to about 500 mg per kg weight of the subject. In some embodiments, the one or more Nur77 antagonists are administered in the form of a pharmaceutical composition. In some embodiments, the method further includes administering to the subject magnesium sulfate and/or betamethasone. In some embodiments, the method further includes administering to the subject one or more supplementary agents. In some embodiments, the one or more supplementary agents is a corticosteroid, an immunosuppressant, an anti-inflammatory agent, an anti-ischemic agent, or a palliative agent.

A kit comprising one or more Nur77 antagonists packaged together with a drug delivery device for administering the one or more Nur77 antagonists to a fetus or a premature baby.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description explain the principles of the invention.

DESCRIPTION OF THE DRAWINGS

This invention is further understood by reference to the drawings wherein.

DETAILED DESCRIPTION OF THE INVENTION

Figure 1:
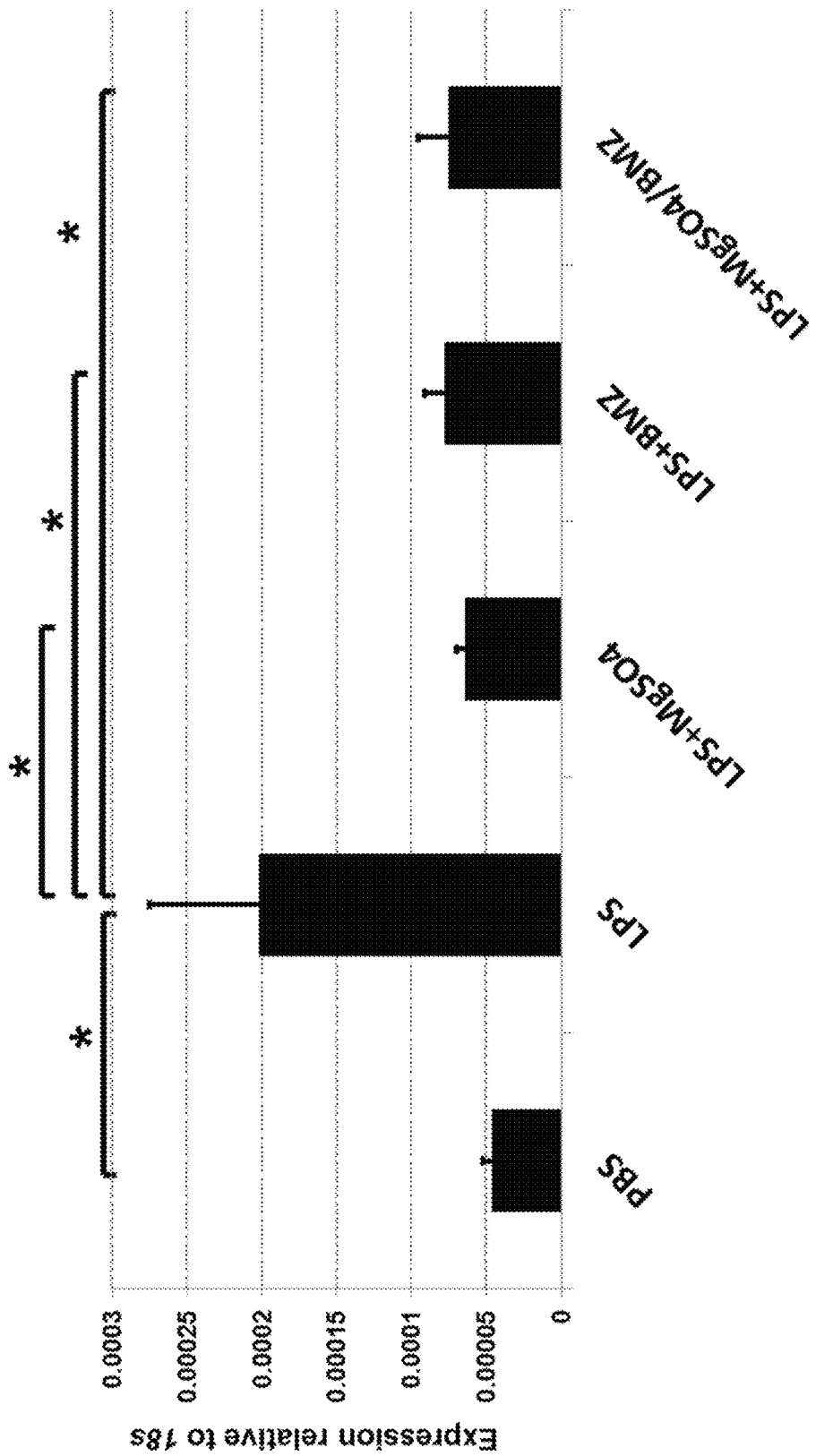
FIG. 1 is a bar graph illustrating Nur77 expression microarray validation. CD1 timed pregnant mice were injected with PBS (controls) or *E. coli* derived lipopolysaccharide (LPS) and normal saline or $MgSO_4$ and/or BMZ on embryonic day E15.5. Brains were collected 6 hours post injections for microarray screening for genes that are upregulated with neuroinflammation and affected by treatments. Screening and the subsequent quantitative real-time PCR (qRT-PCR) validation revealed Nur77 was significantly higher with LPS and declined with $MgSO_4$ and/or BMZ.

Nur77 (also known as Nr4a1) is an orphan nuclear receptor that has been implicated in many processes including inflammation and apoptosis [14-17]. Interestingly, Nur77 has been reported to play opposing roles in both inflammation and apoptosis depending on the context of tissue, disease and injury examined. Such paradigms exist between inflammatory responses stimulated by LPS. For example, Li et al. (2015) observed that inhibition of Nur77 signaling reduced sepsis induced by LPS exposure in adult mice, suggesting that Nur77 plays a central role in global inflammation [18]. In contrast, Hamers et al. (2014) did not observe involvement of Nur77 in the inflammatory response to LPS induced peritonitis [19]. However, in this same study the absence of Nur77 expression resulted in improved pathology, suggesting that Nur77 plays a role in pathogenesis or perhaps the inflammatory influence is transient and undetected. Indeed, transient expression of Nur77 in macrophages is induced upon exposure to LPS in vitro [20]. Such up-regulation of Nur77 expression has also been linked to apoptosis in both macrophages and thymocytes [16, 21].

Although less characterized, Nur77 has been implicated in CNS pathology.

Specifically, Nur77 has been reported to promote cerebral apoptosis that occurs in adult brain injury [22]. This response can be mitigated by the administration of immunosuppressant, suggesting that in addition to apoptosis, Nur77 may also influence neuroinflammation [22-24]. Although Nur77 expression can be detected in the brains of normal adults, Nur77 expression has not been detected in prenatal brains [16].

Therefore, as disclosed herein, an in vivo model of preterm labor [11], [12] and perinatal brain injury and microarray analysis of fetal tissue were used to study the role of Nur77, if any, in perinatal brains, e.g., perinatal brain injury such as perinatal neuroinflammation. In this model, pregnant mice were injected intrauterine with PBS as a vehicle control or *E. coli* lipopolysaccharide (LPS), which invokes inflammation and preterm labor within 6 hours of exposure. Through non-biased microarray screening, it was discovered that a significant increase in the expression of Nur77 was observed in pups exposed to LPS in utero. Additionally, it was discovered that pups of dams treated with $MgSO_4$ and/or BMZ had a significantly decreased expression in Nur77 compared to positive controls. These results were validated via qRT-PCR and were found significantly different between LPS versus control and treatment groups.

These results indicate that Nur77 expression and signaling plays a role in perinatal brain injuries, such as perinatal neuroinflammation, caused by preterm labor and/or preterm birth. As used herein, "preterm birth" in humans refers to delivery before 37 weeks of gestation, and "preterm labor" in humans refers to regular contractions of the uterus, which result in changes in the cervix, that start before 37 weeks of gestation. The average human gestation is about 40 weeks from the woman's last menstrual period. Therefore, absent a commonly accepted time, by those skilled in the art, before which delivery and labor are considered preterm for a given non-human animal, "preterm birth" and "preterm labor" refer to delivery and regular contractions that occur before about completion of 93% of the average gestation period for the species to which the given non-human animal belongs.

Therefore, the present invention relates to manipulating the role of Nur77 in the pathogenesis of preterm labor that is associated with perinatal neuroinflammation to lessen clinical complications and outcomes of preterm labor and/or preterm delivery.

In some embodiments, the present invention relates to preventing, treating, or inhibiting a Nur77 disease or disorder in a subject, which comprises reducing or inhibiting the expression of Nur77 or reducing or inhibiting Nur77 receptor signaling in the subject by administering to the subject a therapeutically effective amount of one or more Nur77 antagonists. In some embodiments, the therapeutically effective amount is a prophylactically effective amount.

As used herein, a "Nur77 disease or disorder" refers to a disease or disorder that is associated with preterm labor and/or preterm birth of the given subject. In some embodiments, a Nur77 disease or disorder is caused by preterm labor and/or preterm birth of the subject. In some embodiments, a Nur77 disease or disorder is caused by an increase in the expression of the Nur77 gene in the subject. In some embodiments, a Nur77 disease or disorder is caused by an increase in the amount of Nur77 in the subject. In some embodiments, the Nur77 disease or disorder is a perinatal brain injury caused by preterm birth and/or preterm labor. Examples of a Nur77 disease or disorder include perinatal neuroinflammation, perinatal neurological injury, vascular injury, neurodevelopmental disabilities, cerebral palsy, and the like.

As used herein, a "Nur77 antagonist" and a "Nr4a1 antagonist" refer to an agent that prevents, inhibits, or reduces the expression of a Nur77 gene and/or prevents, inhibits, or reduces the activity of the protein encoded by the Nur77 gene. A Nur77 antagonist can be a nucleic acid molecule (e.g., a small interfering RNA (siRNA), a micro RNA (miRNA), an antisense oligonucleotide), a protein, a peptidomimetic, an antibody or an antigen-binding fragment (Fab) thereof, a ribozyme, or a small molecule. In some embodiments, a Nur77 antagonist specifically antagonizes the interaction between Nur77 and Liver kinase B1 (LKB1). In some embodiments, a Nur77 antagonist selectively binds the ligand binding domain (LBD) of LKB1. In some embodiments, the Nur77 antagonist is an antibody that specifically binds to Nur77 or LKB1. In some embodiments, the Nur77 antagonist is an antibody that specifically binds to the ligand binding domain (LBD) of LKB1. In some embodiments, a Nur77 antagonist prevents, inhibits, or reduces the interaction between Nur77 and Liver kinase B1 (LKB1). Exemplary Nur77 antagonists include ethyl 2-(2, 3,4-trimethoxy-6-octanoylphenyl)acetate (TMPA), 1,1-Bis (3'-indolyl)-1-(p-substituted phenyl)methane (C-DIM) compounds and analogs thereof (e.g., DIM-C-pPhOH, DIM-C-pPhCO2Me, etc.), and pharmaceutically acceptable salts thereof; hsa-miR-124, hsa-miR-7, and hsa-miR-149; Nur77 siRNA (cat # sc36109, Santa Cruz Biotechnology); and any commercially available antibody that blocks ligand binding, preferably LKB1, to the Nur77. In some embodiments, the Nur77 antagonist is TMPA or a pharmaceutically acceptable salt thereof.

As used herein, "TMPA" refers to ethyl 2-(2,3,4-trimethoxy-6-octanoylphenyl)acetate, which has the following structural formula:

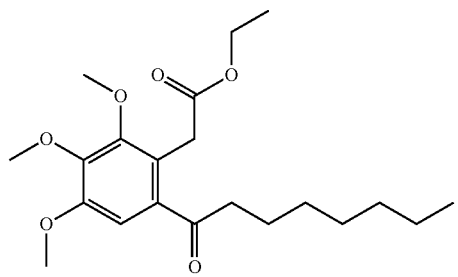 [SMILES: CCCCCCCC(=O)c1cc(OC)c(OC)c(OC)c1CC(=O)OCC]

TMPA is a cell-permeable phenylacetate compound that blocks Nur77 (TR3) LKB1 nuclear-sequestering function by antagonizing the Nur77-LKB1 interaction via direct binding at the LKB1 LBD/ligand binding domain (Kd=0.14 against 5 μM LKB1 binding to 5 μM full-length Nur77).

In some embodiments, the Nur77 antagonists of the present invention are substantially purified. As used herein, a "substantially purified" compound refers to a compound that is removed from its natural environment and/or is at least about 60% free, preferably about 75% free, and more preferably about 90% free, and most preferably about 95-100% free from other macromolecular components or compounds with which the compound is associated with in nature or from its synthesis.

As used herein, a "therapeutically effective amount" refers to an amount of a given agent that may be used to treat, prevent, or inhibit a given disease or condition, such as Nur77 disease or disorder, in a subject as compared to a control. A therapeutically effective amount need not be effective in each and every subject treated or in a majority of treated subjects in a given group or population. Instead, a therapeutically effective amount refers to the amount that effective in the given subject being treated as compared to a control, or the amount presumed to be effective based an amount that is effective in a similarly matched subject. Again, the skilled artisan will appreciate that certain factors may influence the amount required to effectively treat a subject, including the degree of Nur77 disease or disorder, previous treatments, the general health and age of the subject, and the like. Nevertheless, therapeutically effective amounts may be readily determined by methods in the art. It should be noted that treatment of a subject with a therapeutically effective amount may be administered as a single dose or as a series of several doses. The dosages used for treatment may increase or decrease over the course of a given treatment. Optimal dosages for a given set of conditions may be ascertained by those skilled in the art using dosage-determination tests and/or diagnostic assays in the art. Dosage-determination tests and/or diagnostic assays may be used to monitor and adjust dosages during the course of treatment.

In some embodiments, a therapeutically effective amount is a prophylactically effective amount. As used herein, a "prophylactically effective amount" means an amount sufficient to prevent, inhibit, or reduce the likelihood of the onset of a given disease or disorder (e.g., perinatal neuroinflammation), or a symptom or complication thereof in a subject as compared to a control.

Dosing is dependent upon severity and responsiveness of the condition to be treated, with course of treatment lasting from several days to several months or until a reduction of symptoms is achieved. Dosing may be, for example, daily, weekly, or monthly. The actual amount administered, and rate, and time-course of administration, will depend a variety of factors including the nature and severity of the disease or condition being treated, the age, weight, and overall health of the subject being treated, the given Nur77 antagonist and any supplementary agents, the route of administration, and the particular composition and formulation being administered. The dosages and dosing schedule for a given subject may be readily determined by those skilled in the art.

Nevertheless, in some embodiments, the dose of the one or more Nur77 antagonists administered to the subject is about 5 to 500 mg per kg weight of the subject. In some embodiments, the dose of the one or more Nur77 antagonists administered to the subject is about 5 to 500 mg per kg weight of the subject, wherein the subject is a fetus. In some embodiments, the dose of the one or more Nur77 antagonists administered to the subject is about 5 to 500 mg per kg weight of the subject, wherein the subject is a preterm baby. In some embodiments, a dose of the one or more Nur77 antagonists of about 5 to 500 mg per kg weight of the mother and the subject is administered to the mother. In some embodiments, the subject is administered a dose before, during, and/or after preterm labor. In some embodiments, the subject is administered a dose before, during, and/or after preterm birth. In some embodiments, the subject is administered a dose during preterm labor. In some embodiments, the subject is administered a dose after preterm birth. In some embodiments, the dose administered to the subject is a therapeutically effective amount.

In some embodiments, the route of administration of the one or more Nur77 antagonists is intraarterial, intraarticular, intramuscular, intraperitoneal, intrathecal, intrauterine, or intravenous. In some embodiments, the route of administration of the one or more Nur77 antagonists is by perfusion. In some embodiments, the route of administration of the one or more Nur77 antagonists is by intrauterine injection. In some embodiments, the one or more Nur77 antagonists are delivered to the subject via an umbilical venous catheter. In some embodiments, the one or more Nur77 antagonists are locally administered. In some embodiments, the one or more Nur77 antagonists are administered to the subject within 12 hours after birth. In some embodiments, the one or more Nur77 antagonists are administered to the subject within 6 hours after birth. In some embodiments, the one or more Nur77 antagonists are administered to the subject within 3 hours after birth. In some embodiments, the one or more Nur77 antagonists are administered to the subject within an hour, preferably within 45 minutes, more preferably within 30 minutes, more preferably within 15 minutes after birth.

In some embodiments, the subject is a fetus. In some embodiments, the fetus is treated in utero. In some embodiments, the fetus is treated in utero by administering the one or more Nur77 antagonists to the mother. In some embodiments, the subject is a premature baby. As used herein, a "premature baby" refers to a baby whose birth was a preterm birth. In some embodiments, the subject is human.

In some embodiments, the subject is in need thereof. As used herein, a subject "in need thereof" refers to a subject who has or is likely to have a Nur77 disease or disorder. In some embodiments, the subject in need thereof is the fetus of a mother who is having preterm labor, had preterm labor, and/or is likely to have preterm labor. In some embodiments, the subject in need thereof is the fetus of a mother who had, has, and/or is likely to have inflammation of the uterus. In some embodiments, the subject in need thereof is a premature baby. In some embodiments, the subject in need thereof is one who is diagnosed as having a high expression level of Nur77 as compared to a control group of healthy subjects who are otherwise similarly situated.

In some embodiments, the one or more Nur77 antagonists are co-administered with one or more supplementary agents. The one or more supplementary agents may be administered before, at the same time as, or after administration of a Nur77 antagonist. In some embodiments, the supplementary agent is a corticosteroid, an immunosuppressant, an anti-inflammatory agent, an anti-ischemic agent, or a palliative agent. In some embodiments, the one or more Nur77 antagonists and the one or more supplementary agents are administered together as a single formulation.

In some embodiments, the Nur77 antagonist is TMPA or a pharmaceutically acceptable salt thereof. In some embodiments, TMPA or a pharmaceutically acceptable salt thereof is administered as oral capsule or tablet containing about 50 mg, about 100 mg, about 250 mg, about 200 mg, about 225 mg, about 250 mg, about 300 mg, about 400 mg, about 500 mg or about 600 mg, about 700 mg or about 800 mg of the active ingredient.

Compositions

In some embodiments, the one or more Nur77 antagonists are administered in the form of a pharmaceutical composition. Compositions of the present invention, including pharmaceutical compositions, comprise, consist essentially of, or consists of one or more Nur77 antagonists. As used herein, the phrase "consists essentially of" in the context of a composition containing one or more Nur77 antagonists means that the composition may comprise one or more supplementary agents, binders, adjuvants, adsorption delaying agents, antibacterial agents, antifoaming agents, antifungal agents, antioxidants, buffering agents, diluents, disintegration agents, dispersing agents, emulsifying agents, erosion facilitators, filling agents, flavoring agents, lubricants, pH adjusting agents, pharmaceutically acceptable carriers, plasticizers, preservatives, solubilizers, stabilizers, surfactants, suspending agents, thickening agents, viscosity enhancing agents, wetting agents, and the like, and so long as the additional ingredients do not interfere with the activity of the one or more Nur77 antagonists. A composition that consists of one or more Nur77 antagonists is one which comprises the one or more Nur77 antagonists as the sole active ingredient, i.e., the composition does not contain any supplementary agents, but may include ingredients typically used in pharmaceutical compositions, e.g., binders, adjuvants, adsorption delaying agents, antibacterial agents, antifoaming agents, antifungal agents, antioxidants, buffering agents, diluents, disintegration agents, dispersing agents, emulsifying agents, erosion facilitators, filling agents, flavoring agents, lubricants, pH adjusting agents, pharmaceutically acceptable carriers, plasticizers, preservatives, solubilizers, stabilizers, surfactants, suspending agents, thickening agents, viscosity enhancing agents, wetting agents, and the like.

The term "pharmaceutical composition" refers to a composition suitable for pharmaceutical use in a subject. A pharmaceutical composition generally comprises an effective amount of an active agent, e.g., one or more Nur77 antagonists according to the present invention, and a pharmaceutically acceptable carrier. The term "effective amount" refers to a dosage or amount sufficient to produce a desired result. The desired result may comprise an objective or subjective improvement in the recipient of the dosage or amount, e.g., long-term survival, effective prevention of a disease state, and the like.

Pharmaceutical compositions according to the present invention may further include one or more supplementary agents. Pharmaceutical compositions according to the present invention may further include one or more supplementary agents. Similarly, in some embodiments, treatments according to the present invention include co-administering one or more Nur77 antagonist with one or more supplementary agents. The one or more supplementary agents may be administered before, at the same time as, or after administration of a Nur77 antagonist. Examples of suitable supplementary agents include corticosteroids, immunosuppressants, anti-inflammatory agents, anti-ischemic agents, and/or palliative agents.

Exemplary corticosteroids include (steroid receptor agonists) such as budesonide, prednisone, and flunisolide.

Exemplary anti-inflammatory agents include steroidal and non-steroidal anti-inflammatory drugs (NSAIDs). Exemplary NSAIDs include, without limitation, ibuprofen (2-(isobutyl phenyl)-propionic acid); methotrexate (N-[4-(2,4 diamino 6-pteridinyl-methyl]methylamino]benzoyl)-L-glutamic acid); aspirin (acetylsalicylic acid); salicylic acid; diphenhydramine (2-(diphenyl methoxy)-N,N-dimethyl ethylamine hydrochloride); naproxen (2-naphthaleneacetic acid, 6-methoxy-9-methyl-, sodium salt, (–)); ketorolac (1H-Pyrrolizine-1-carboxylic acid, 2,3-dihydro-5-benzoyl-, (+-)); phenylbutazone (4-butyl-1,2-diphenyl-3,5-pyrazolidinedione); sulindac-(2)-5-fluoro-2-methyl-1-[[p-(methylsulfinyl)phenyl]methylene-]-1-H-indene-3-acetic acid; diflunisal (2',4',-difluoro-4-hydroxy-3-biphenylcarboxylic acid; piroxicam (4-hydroxy-2-methyl-N-2-pyridinyl-2H-1,2-benzothiazine-2-carboxamide 1,1-dioxide, an oxicam; indomethacin (1-(4-chlorobenzoyl)-5-methoxy-2-methyl-H-indole-3-acetic acid); meclofenamate sodium (N-(2,6-dichloro-m-tolyl)anthranilic acid, sodium salt, monohydrate); ketoprofen (2-(3-benzoylphenyl)-propionic acid; tolmetin sodium (sodium 1-methyl-5-(4-methylbenzoyl-1H-pyrrole-2-acetate dihydrate); diclofenac sodium (2-[(2,6-dichlorophenyl)amino]benzeneatic acid, monosodium salt); hydroxychloroquine sulphate (2-{[4-[(7-chloro-4-quinolyl)amino]pentyl]ethylamino}ethanol sulfate (1:1); penicillamine (3-mercapto-D-valine); flurbiprofen ([1,1-b]phenyl]-4-acetic acid, 2-fluoro-alphamethyl-, (+-)); cetodolac (1-8-diethyl-13,4,9, tetrahydropyrano-[3-4-13]indole-1-acetic acid; mefenamic acid (N-(2,3-xylyl)anthranilic acid; and diphenhydramine hydrochloride (2-diphenyl methoxy-N,N-di-methylethamine hydrochloride). Exemplary, anti-inflammatory agents also include flunisolide hydrofluoroalkane, estrogen, progesterone, dexamethasone, and loteprednol; beta-agonists (e.g., short or long-acting) such as bambuterol, formoterol, salmeterol, and albuterol; anticholinergics such as ipratropium bromide, oxitropium bromide, cromolyn, and calcium-channel blocking agents; antihistamines such as terfenadine, astemizole, hydroxyzine, chlorpheniramine, tripelennamine, cetirizine, desloratadine, mizolastine, fexofenadine, olopatadine hydrochloride, norastemizole, levocetirizine, levocabastine, azelastine, ebastine, and loratadine; antileukotrienes (e.g., anti-cysteinyl leukotrienes (CysLTs)) such as oxatomide, montelukast, zafirlukast, and zileuton; phosphodiesterase inhibitors (e.g., PDE4 subtype) such as ibudilast, cilomilast, BAY 19-8004, theophylline (e.g., sustained-release) and other xanthine derivatives (e.g., doxofylline); thromboxane antagonists such as seratrodast, ozagrel hydrochloride, and ramatroban; prostaglandin antagonists such as COX-1 and COX-2 inhibitors (e.g., celecoxib and rofecoxib), aspirin; and potassium channel openers.

Exemplary immunosuppressants rapamycin, cyclosporine, and the like.

Exemplary anti-ischemic agents include aspirin, Losartan, and the like.

Exemplary palliative agents include dexamethasone, prednisone, and the like.

Pharmaceutical compositions of the present invention may be formulated for the intended route of delivery using methods known in the art. The Nur77 antagonists and pharmaceutical compositions may be administered to a subject by any suitable route, including buccal, cutaneous, inhalation, intraarterial, intracranial, intralesional, intramuscular, intranasal, intraocular, intraperitoneal, intrasynovial, intrathecal, intravascular, intravenous, oral, pulmonary, rectal, subcutaneous, sublingual, topical, transdermal, transmucosal, and vaginal administration. In some embodiments, the administration is local. In some embodiments, the administration is systemic. In some embodiments, the administration is enteral. In some embodiments, the administration is parenteral. In some embodiments, the administration is topical. The preferred route of administration and pharmaceutical formulation will vary with the condition and age of the subject, the nature of the condition to be treated, the therapeutic effect desired, and the particular Nur77 antagonist used, and can be readily determined by those skilled in the art.

Pharmaceutical compositions according to the present invention may include one or more of the following: binders, adjuvants, adsorption delaying agents, antibacterial agents, antifoaming agents, antifungal agents, antioxidants, buffering agents, diluents, disintegration agents, dispersing agents, emulsifying agents, erosion facilitators, filling agents, flavoring agents, lubricants, pH adjusting agents, pharmaceutically acceptable carriers, plasticizers, preservatives, solubilizers, stabilizers, surfactants, suspending agents, thickening agents, viscosity enhancing agents, wetting agents, and the like. The pharmaceutical compositions may be formulated as solutions, liposomes, nanoparticles, dispersions, suspensions, emulsions, powders for reconstitution, solids, and the like. The compositions and formulations of the present invention may be optimized for increased stability and efficacy using methods in the art. See, e.g., Carra et al. (2007) Vaccine 25:4149-4158, which is herein incorporated by reference. In some embodiments, the pharmaceutical compositions are provided as controlled release formulations. Suitable controlled release formulations known in the art can be readily selected by those skilled in the art for administering to a subject one or more Nur77 antagonists according to a desired drug release profile.

As used herein, a "pharmaceutically acceptable vehicle" or "pharmaceutically acceptable carrier" are used interchangeably and refer to solvents, dispersion media, coatings, and the like, that are compatible with pharmaceutical administration and comply with the applicable standards and regulations, e.g., the pharmacopeial standards set forth in the United States Pharmacopeia and the National Formulary (USP-NF) book, for pharmaceutical administration. Thus, for example, unsterile water is excluded as a pharmaceutically acceptable carrier for, at least, intravenous administration. Pharmaceutically acceptable vehicles include those known in the art. See, e.g., REMINGTON: THE SCIENCE AND PRACTICE OF PHARMACY. 20$^{th}$ ed. (2000) Lippincott Williams & Wilkins. Baltimore, Md., which is herein incorporated by reference. Exemplary pharmaceutically acceptable carrier materials include acacia, calcium glycerophosphate, calcium lactate, carrageenan, cellulose and cellulose conjugates, cholesterol, cholesterol esters, colloidal silicon dioxide, diglyceride, dipotassium phosphate, gelatin, glycerin, magnesium silicate, maltodextrin, monoglyceride, phosphotidylcholine, polyvinylpyrrollidone (PVP), pregelatinized starch, sodium caseinate, sodium chloride, soy lecithin, sugars sodium stearoyl lactylate, taurocholic acid, tricalcium phosphate, and the like.

The pharmaceutical compositions of the present invention may be provided in dosage unit forms. As used herein, a "dosage unit form" refers to physically discrete units suited as unitary dosages for the subject to be treated; each unit containing a predetermined quantity of the one or more Nur77 antagonists calculated to produce the desired therapeutic effect in association with the required pharmaceutically acceptable carrier. The specification for the dosage unit forms of the invention are dictated by and directly dependent on the unique characteristics of the given Nur77 antagonist and desired therapeutic effect to be achieved, and the limitations inherent in the art of compounding such an active compound for the treatment of individuals.

Toxicity and therapeutic efficacy of Nur77 antagonists according to the instant invention and compositions thereof can be determined using cell cultures and/or experimental animals and pharmaceutical procedures in the art. For example, one may determine the lethal dose, $LC_{50}$ (the dose expressed as concentration×exposure time that is lethal to 50% of the population) or the $LD_{50}$ (the dose lethal to 50% of the population), and the $ED_{50}$ (the dose therapeutically effective in 50% of the population) by methods in the art. The dose ratio between toxic and therapeutic effects is the therapeutic index and it can be expressed as the ratio $LD_{50}/ED_{50}$. Nur77 antagonists which exhibit large therapeutic indices are preferred. While Nur77 antagonists that result in toxic side-effects may be used, care should be taken to design a delivery system that targets such compounds to the site of treatment to minimize potential damage to uninfected cells and, thereby, reduce side-effects.

The data obtained from the cell culture assays and animal studies can be used in formulating a range of dosages for use in humans. Preferred dosages provide a range of circulating concentrations that include the $ED_{50}$ with little or no toxicity. The dosage may vary depending upon the dosage form employed and the route of administration utilized. Therapeutically effective amounts and dosages of one or more Nur77 antagonists according to the present invention can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography. Additionally, a dosage suitable for a given subject can be determined by an attending physician or qualified medical practitioner, based on various clinical factors.

Kits

In some embodiments, the present invention provides a kit comprising one or more Nur77 antagonists or compositions thereof packaged together. In some embodiments, one or more Nur77 antagonists are packaged together with one or more reagents for assaying the level of Nur77 expression. In some embodiments, one or more Nur77 antagonists are packaged together with one or more supplementary agents. One or more components of a kit according to the present invention can be enclosed within an individual container. In some embodiments, the kits comprise the one or more Nur77 antagonists, optionally in one or more unit dosage forms, packaged together as a pack and/or in drug delivery device, e.g., a pre-filled syringe. In some embodiments, the kits comprise one or more Nur77 antagonists packaged together with a device for intrauterine delivery. In some embodiments, the kits comprise one or more Nur77 antagonists packaged together with an umbilical venous catheter. In some embodiments, the kits include a carrier, package, or container that may be compartmentalized to receive one or more containers, such as vials, tubes, and the like.

Kits of the invention can include labels or inserts. In some embodiments, kits according to the present invention include a label or packaging insert including a description of the components or instructions for use in vitro, in vivo, or ex vivo, of the components therein. Labels or inserts include "printed matter", e.g., paper or cardboard, or separate or affixed to a component, a kit or packing material (e.g., a box), or attached to an ampule, tube or vial containing a kit component. In some embodiments, the kits include information prescribed by a governmental agency that regulates the manufacture, use, or sale of compounds and compositions according to the present invention. Labels or inserts can additionally include a computer readable medium, such as a disk (e.g., hard disk), optical disk such as CD- or DVD-ROM/RAM, DVD, MP3, magnetic tape, or an electrical storage media such as RAM and ROM or hybrids of these such as magnetic/optical storage media, FLASH media or memory type cards. In some embodiments, the kits are designed for cold storage.

EXAMPLES

The following examples are intended to illustrate but not to limit the invention.

Example 1: Materials and Methods

Mice Arrival and Acclimation

CD1 timed pregnant mice were purchased from Harlan Laboratories (Indianapolis, Ind.) or similar vendor. Because of the requirement of a three- to seven-day acclimation period upon arrival, pregnant dams were delivered at a time that took into consideration the acclimation period and so that experimentation began on gestation day E15. Typically, dams bred 10-14 days prior to shipping were used. Animals arrived in shipments of 12-15 to accommodate all injections and tissue collection.

Inflammatory Model

Mice were randomly assigned to six groups: Group 1) 4 pups/PBS+normal saline (NS), Group 2) 4 pups/LPS+NS, Group 3) 4 pups/LPS+MgSO$_4$, Group 4) 4 pups/LPS+BMZ, Group 5) 4 pups/LPS+MgSO$_4$ and BMZ, and Group 6) 4 pups/LPS+TMPA. Except for the non-surgical control (Group 1), each group underwent intrauterine injection of either vehicle or LPS. Phosphate buffered saline (PBS) and normal saline (NS) were used for the control groups. LPS in combination with MgSO$_4$, BMZ, MgSO$_4$ and BMZ, or TMPA were used in the experimental groups. Mice received 300 µl of normal saline prior to surgery as a precaution against dehydration. All surgical procedures were performed under anesthesia with isoflurane within a sterile environment using PPE and sterile surgical tools to prevent infection. E15.5 pup brains were compared 6 hours post LPS within the six treatment groups as described in Table 1:

TABLE 1

Pup Brain Groups

| Groups | Collected E15.5 at 6 hours Post Injury |
|---|---|
| 1 | PBS + normal saline (NS) |
| 2 | LPS + NS |
| 3 | LPS + MgSO$_4$ |
| 4 | LPS + BMZ |
| 5 | LPS + MgSO$_4$ and BMZ |
| 6 | LPS + TMPA |

Therapeutic Intervention

Mice randomized to Groups 3-5 received a single subcutaneous (SQ) injection of 0.1 mg of MgSO$_4$ and/or BMZ 30 minutes after intrauterine injection of LPS, per the Hallak protocol [35]: 270 mg/kg SQ loading dose followed by 27 mg/kg SQ every 20 minutes for a four-hour duration. Mice randomized to Group 6 received a single dose of 50 mg/kg TMPA (approximately 2 mg of TMPA in 80 µl dimethyl sulfoxide (DMSO)) 30 minutes post-operative, as described by Zhan et al. [14].

Post-Surgical Care

At six hours post-operative, animals were euthanized under isoflurane anesthesia via cervical dislocation by trained staff and tissue collected by a member of the protocol team.

Fetal Brain Harvest

Immediately, after euthanasia, fetal tissue was collected for endpoint analysis. The brains of animals selected for molecular analysis were extracted and immediately frozen with liquid nitrogen for subsequent storage in −80° C. Animals selected for histology underwent whole body fixation as described by Ward et al., 2012 [19].

Tissue Collection

Whole brains were collected following euthanasia six hours post-operatively on the four pups close to the injection site selected for qRT-PCR, tissue culture and cytokine assessment. The entire pup was fixed for histological analysis for those selected for microscopy. Tissue from all subjects was collected and stored for future use.

Data Analysis

A power analysis was conducted to determine the appropriate number of subjects. Using data, it was determined that a minimum number of pups per treatment group of 5 was necessary to obtain statistical power at the 0.80 level. This translated to 2 dams/group for a total request of 25 dams. Results were analyzed and statistical significances between groups was determined using a student's t-test.

Example 2: Role of Nur77 in Perinatal Brain Injury

To examine the role of Nur77 in perinatal brain injury, a two-prong approach was utilized in an in vivo murine model of intrauterine LPS induced preterm labor and neuroinflammation: (i) Complete absence of Nur77 expression in knockout (KO) mice [26] and (ii) Pharmacological ablation using the Nur77 antagonist, ethyl 2-[2,3,4-trimethoxy-6-(1-octanoyl) phenyl] acetate (TMPA) [25].

The role of Nur77 signaling was evaluated in a genetically ablated mouse model (Nur77 KO). KO models in which specific genes are deleted have been invaluable for elucidating the necessity and function of specific proteins [28].

C57B/6 Nur77 KO mice and wild-type (WT controls) were acquired from Jackson Labs (catalog numbers 006187 and 000664). Once acclimated, at approximately 2 weeks, animals were bred as their respective genotype: KO male× KO female and WT male×WT female. Ordering and mating were staggered so that no more than 10 surgeries occurred daily. Once more, E15.5 pup brains were compared at 6 hours post LPS. Standard operating procedures were approved by IACUC prior to the onset of breeding.

For CD1 mice, E15.5 collected 6 hours post LPS dosing with 100 µg per 40 grams dam weight were used. 100 µg of LPS induced a comparable inflammatory response within 6 hours for CD1 mice, analogous to results by Burd et al. [5], [6], and [36]. However, Nur77 KO mice and WT controls are on a C57BL/6 genetic background that is more tolerant to LPS injury. Previous reports indicate that 250 µg per dam induced neuroinflammation with 6 hours at E15.5 in mice from the C57BL/6 background. [5] [6]. In contrast, severe necrosis was observed in earlier studies within 6 hours of injection with 250 µg LPS in CD1 mice. Therefore, Nur77 KO mice and WT controls received a higher dose of LPS, 250 µm per 40 grams dam weight. Despite dosage differences, the reproducibility of the neuroinflammatory phenotype permits meta-analyses and retrospective comparisons between studies that analyze neuroinflammation at E15.5.

At E.15.5, Nur77 KO and WT control dams were randomized to receive intrauterine injection of either vehicle (PBS as a control group) or LPS from *Escherichia coli*. Animals received intrauterine LPS in 100 µl of PBS in the experimental injury groups.

Microarray Validation of Nur77 Expression

CD1 timed pregnant mice were injected with PBS (controls) or LPS and normal saline or MgSO$_4$ and/or BMZ on embryonic day E15.5. Brains were collected 6 hours post injections for microarray screening for genes that are upregulated with neuroinflammation and affected by treatment.

Screening and qRT-PCR validation revealed Nur77 was significantly higher with LPS but lower with MgSO$_4$ and/or BMZ. See FIG. 1. Gene expression of fetal brain tissue was examined and demonstrated a four-fold increase in Nur77 expression compared to the control. Treatment with MgSO$_4$, BMZ, or combination therapy significantly reduced the expression of Nur77. Quantitative reverse-transcriptase PCR analysis was used to validate microarray results. Results confirmed that Nur77 expression was significantly elevated with LPS and reduced with either MgSO$_4$ or MBZ treatments. *p<0.04 by student's t-test.

Nur77 KO Mice Exhibited Reduced Neuroinflammatory Expression

Figure 2:
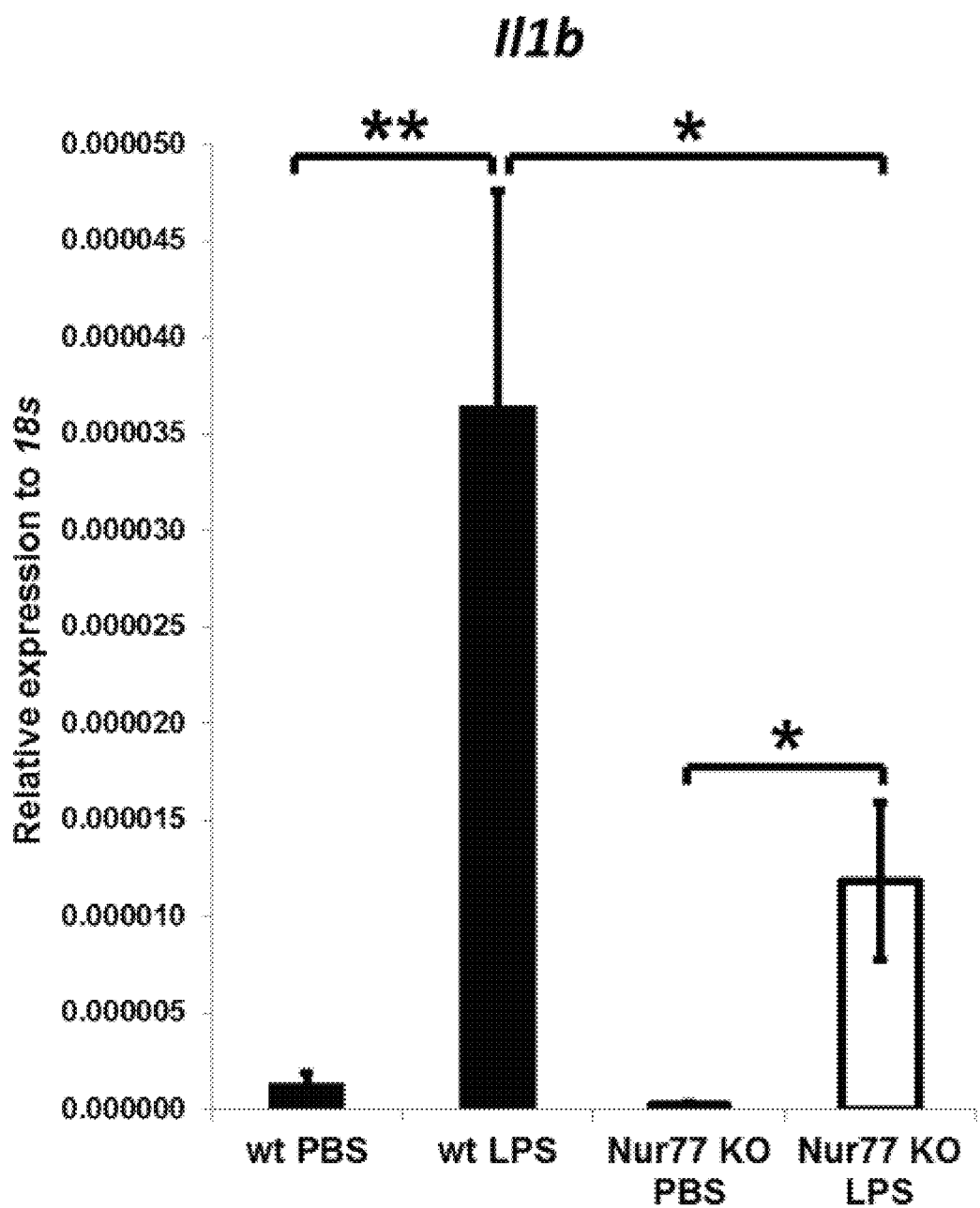
FIG. 2 to FIG. 5 are bar graphs illustrating Nur77 KO mice that exhibit reduced neuroinflammatory expression. Timed pregnant C56BL/6 wild-type (WT) mice versus Nur77 knock-out (KO) mice were injected with PBS (controls) or LPS and normal saline on embryonic day E15.5. Brains were collected 6 hours post injections for qRT-PCR analysis of inflammatory related genes Il1b (FIG. 2), Il6 (FIG. 3), Tlr4 (FIG. 4), and Tnfa (FIG. 5).
Figure 3:
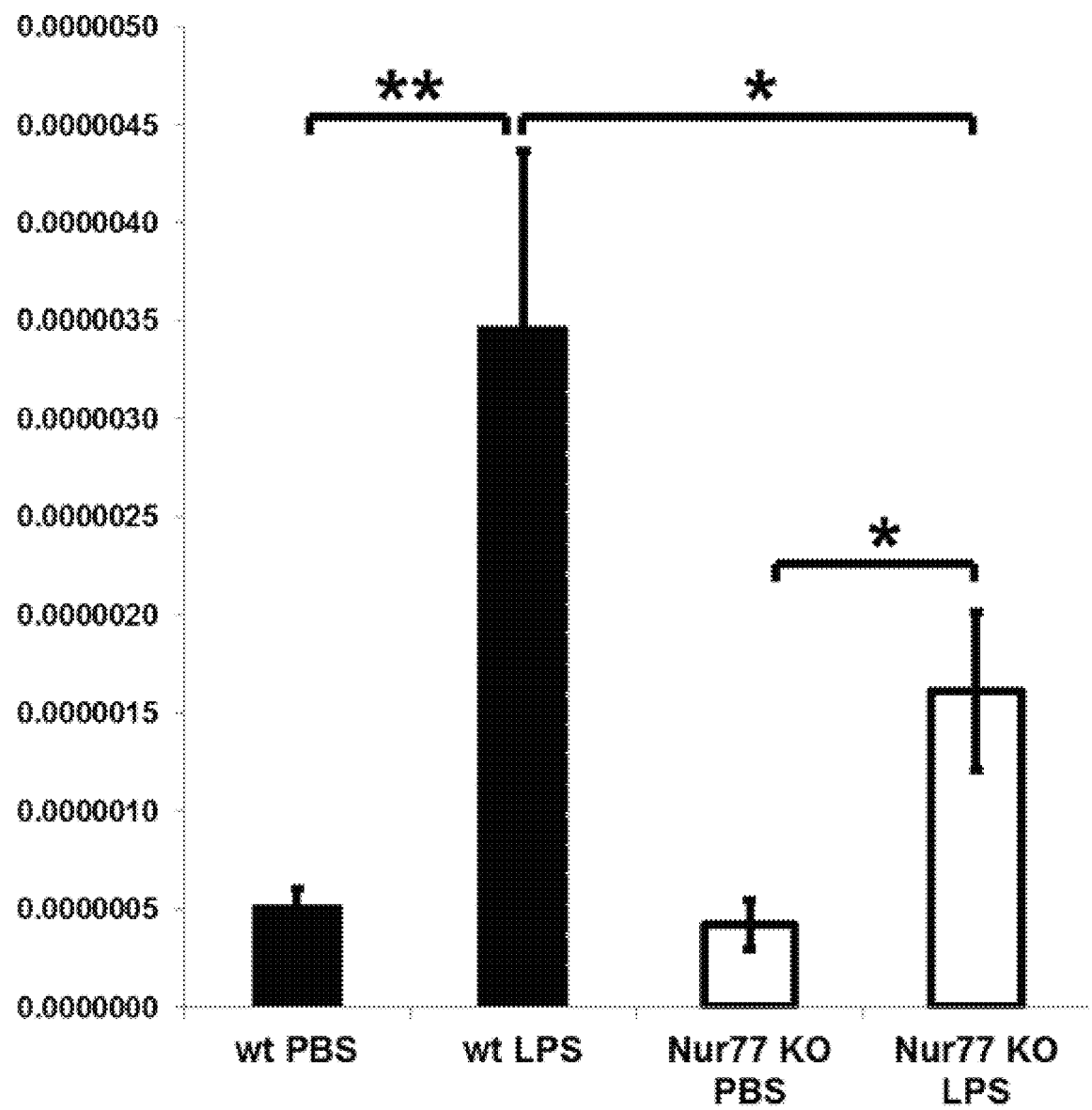
Figure 4:
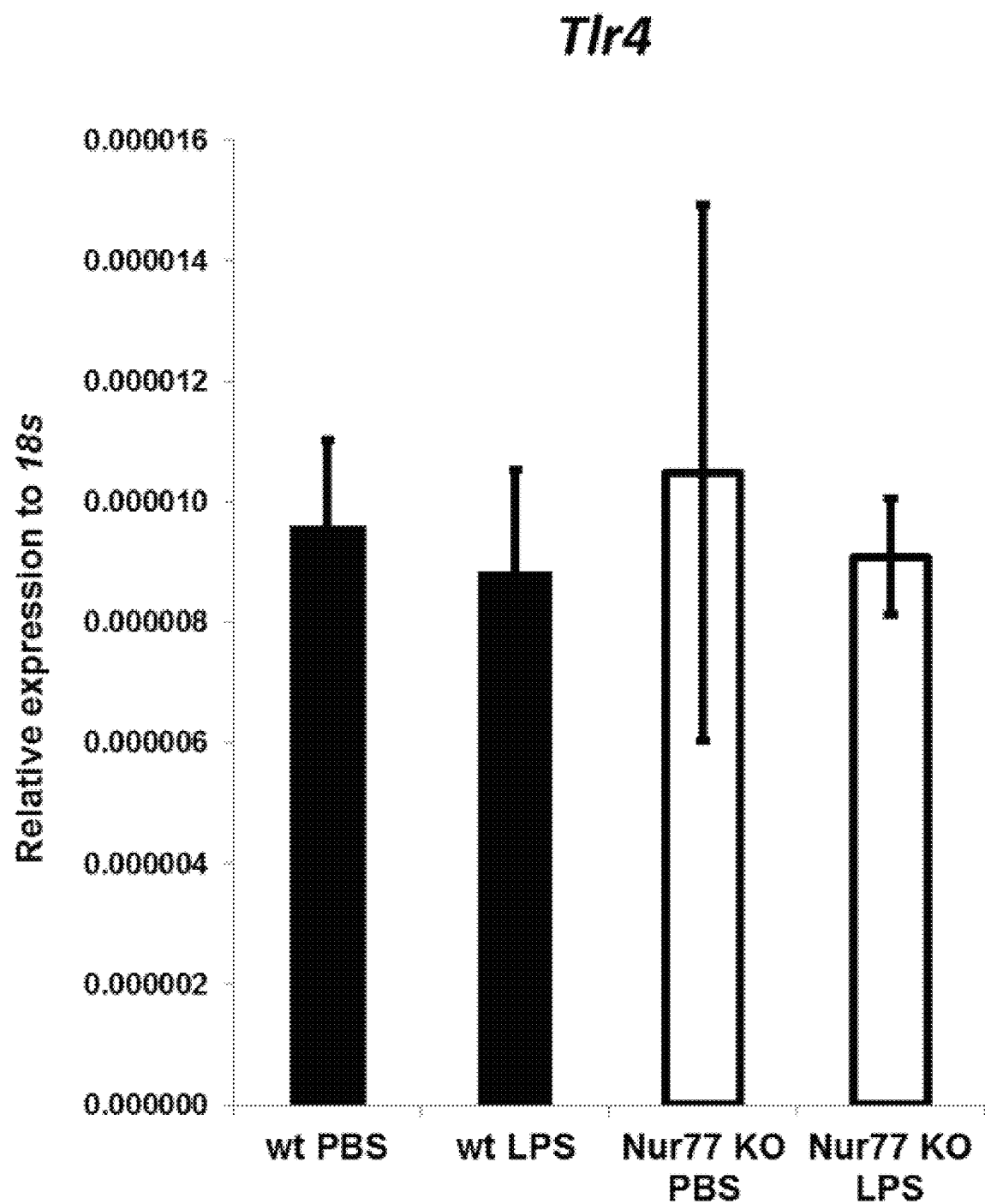
Figure 5:
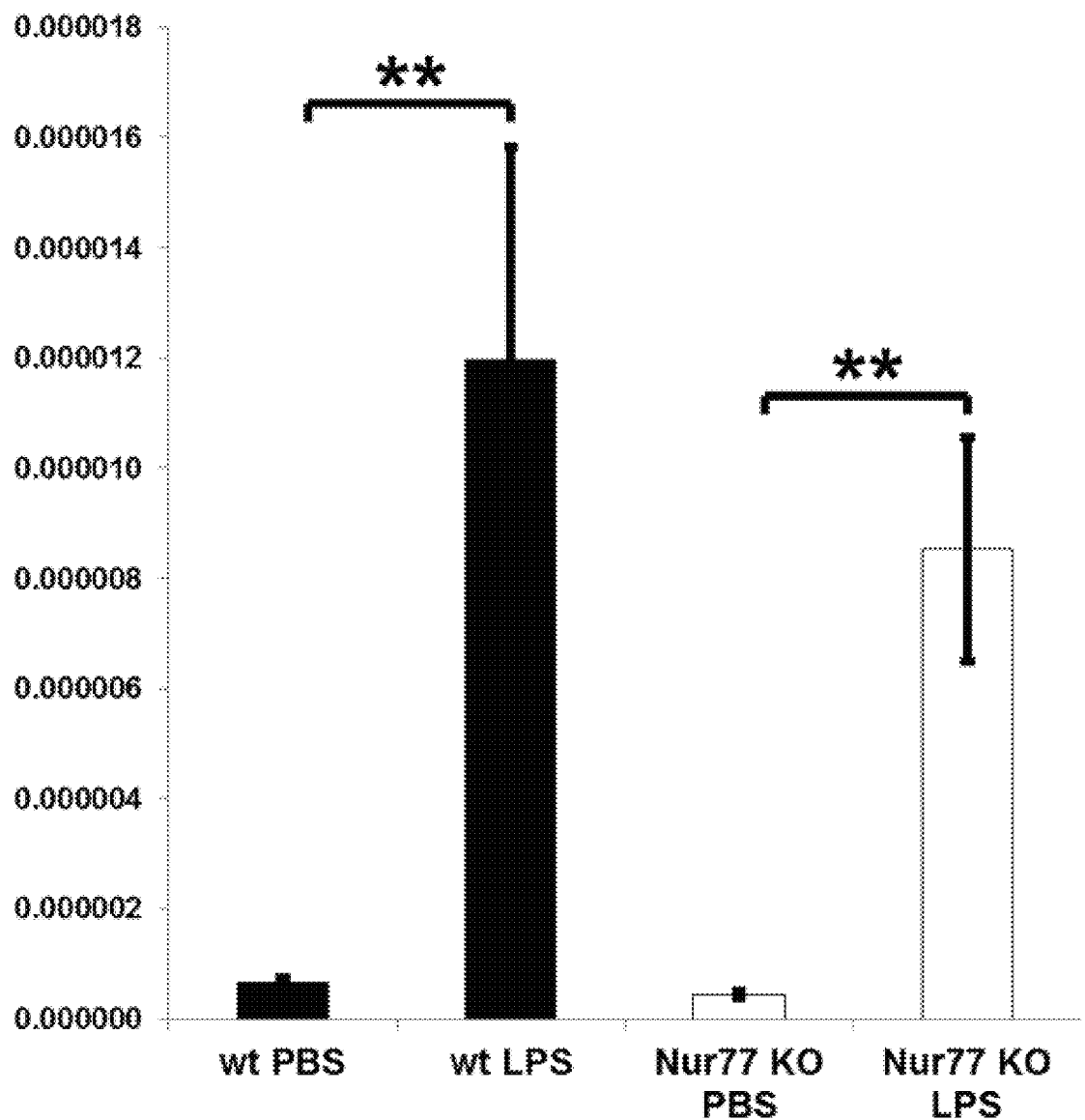
Figure 6:
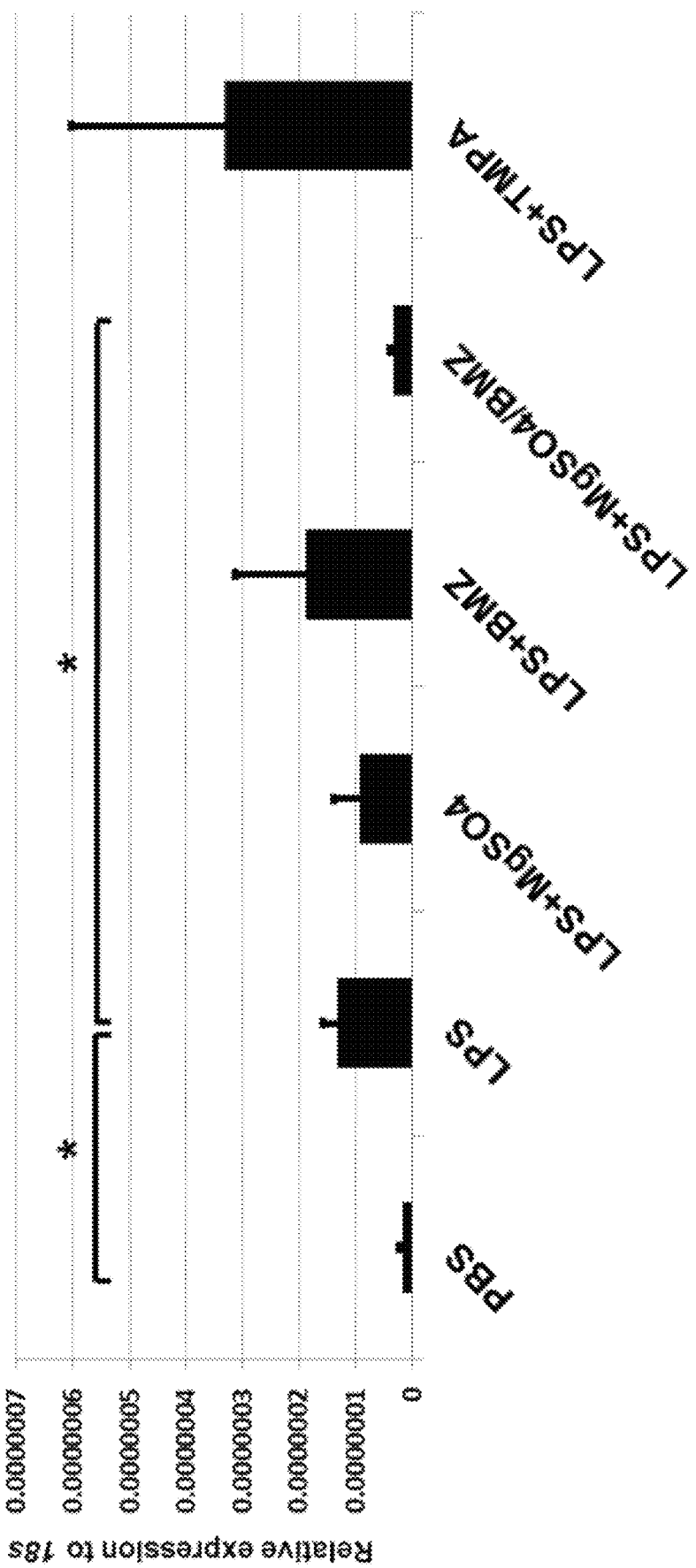
FIG. 6 to FIG. 10 are bar graphs illustrating a comparison of the effects of $MgSO_4$, BMZ, and Nur77 antagonist TMPA on perinatal neuroinflammation. CD1 timed pregnant mice were injected with PBS (controls) or LPS and normal saline or $MgSO_4$ and/or BMZ or TMPA on embryonic day E15.5. Brains were collected 6 hours post injections for expression analysis of neuroinflammatory genes Il1b (FIG. 6), Tnfa (FIG. 7), Ccr2 (FIG. 8), Ikbkb (FIG. 9), and Nos2 (FIG. 10) by qRT-PCR.
Figure 7:
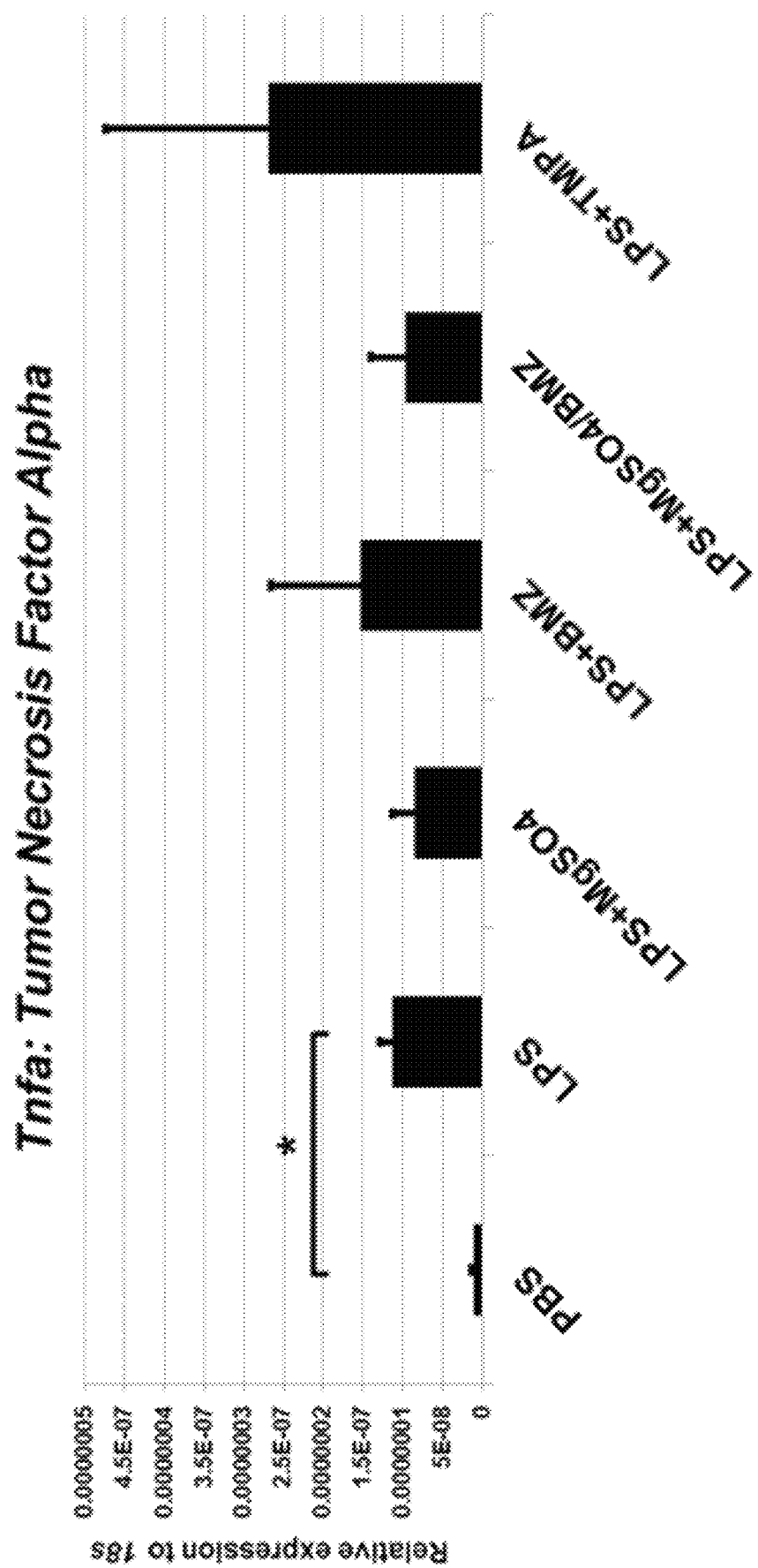
Figure 8:
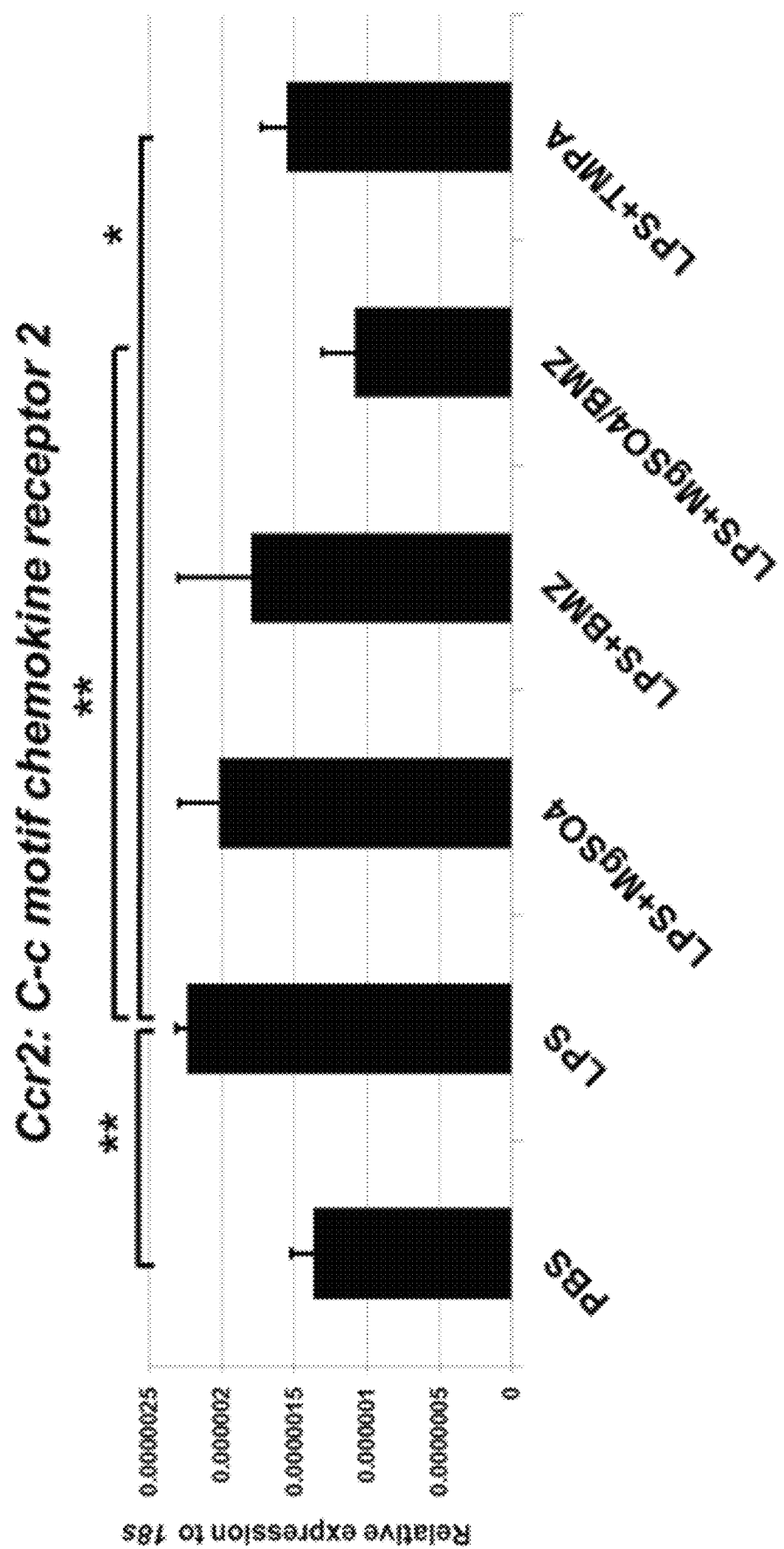
Figure 9:
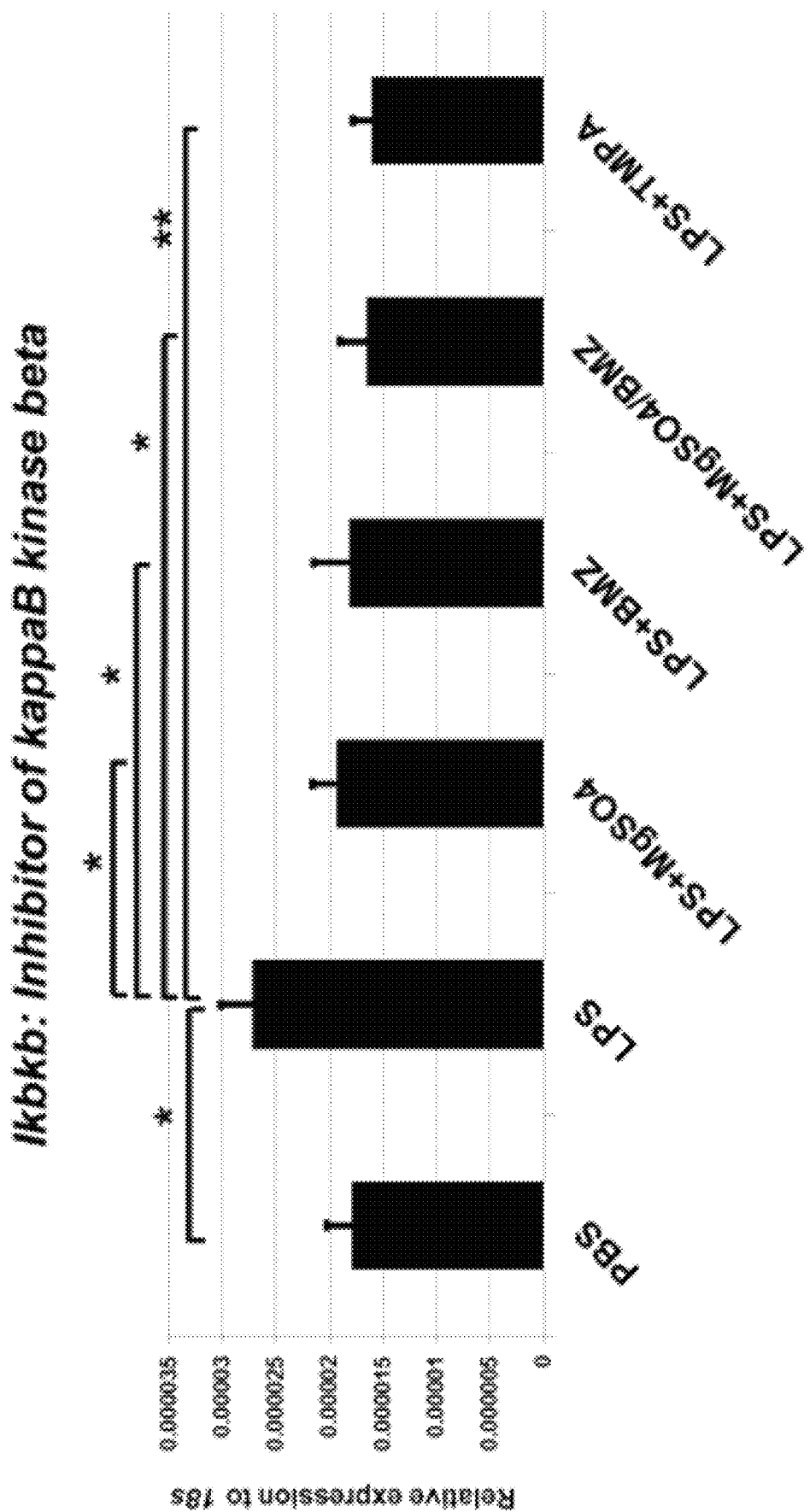
Figure 10:
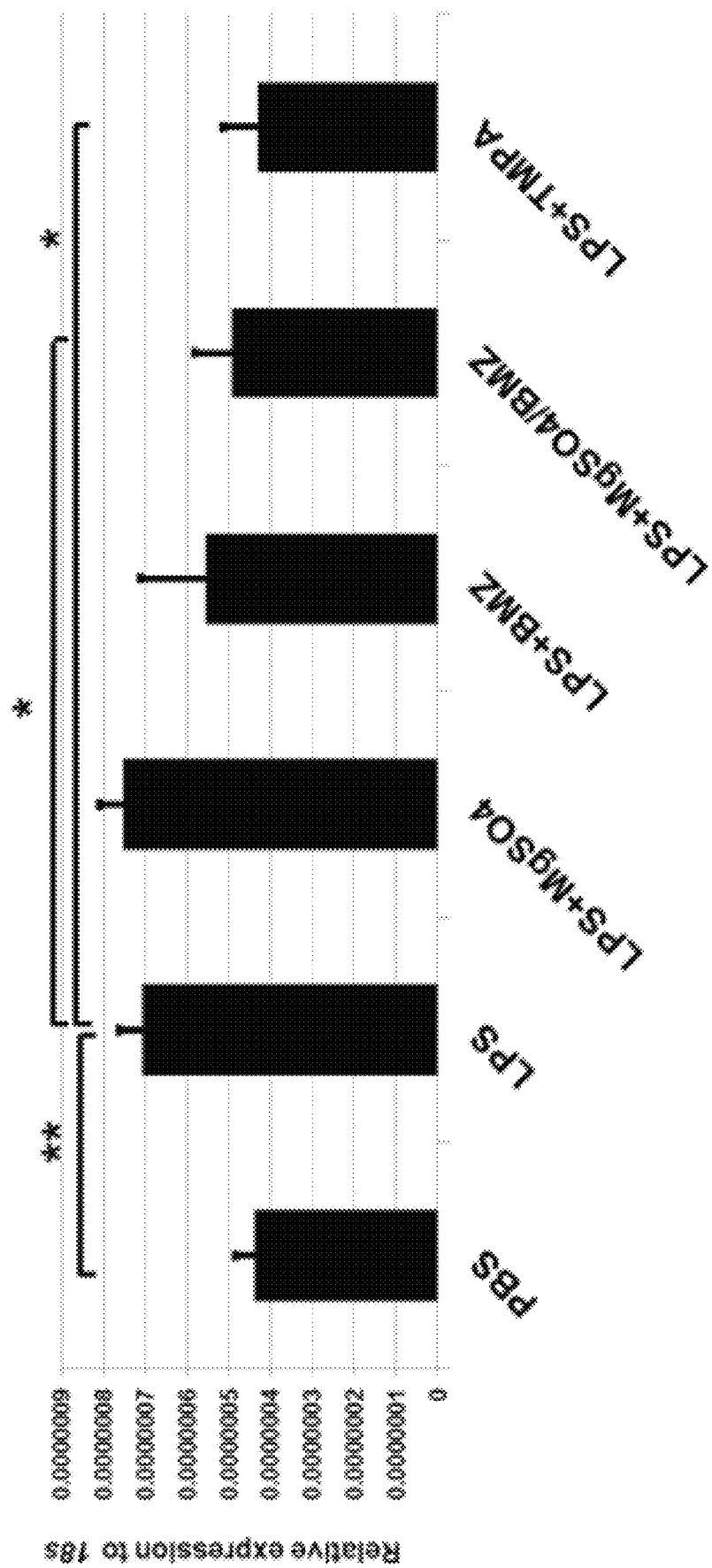

A comparison between the WT and Nur77 KO mice revealed an even greater perturbation of inflammatory gene expression from LPS. Timed pregnant WT mice and Nur77 KO mice were injected with PBS (controls) or LPS and normal saline on embryonic day E15.5. Brains were collected 6 hours post injections for qRT-PCR analysis of inflammatory related genes Il1b, Il6, Tlr4, and Tnfa. In embryo brains from Nur77 KO mice exposed to LPS displayed significant reduction in Il1b and Tnfa expression. See FIG. 2 and FIG. 5. Interleukin 6 (Il6) expression was also significantly reduced, whereas Toll like receptor 4 (Tlr4) was not different between groups. See FIG. 3 and FIG. 4.

Pharmacological Ablation

TMPA is an agent that binds to Nur77 at the LKB1 ligand binding domain and inhibits its expression. TMPA has been used in prior research to blunt the effects of Nur77 in the context of glucose metabolism in mice with demonstrated efficacy [25]. Treatment with TMPA was compared in parallel to $MgSO_4$ and/or BMZ treatments in normal outbred mice following the experimental procedures described above.

As shown in FIG. 6 to FIG. 10, Nur77 expression was significantly higher with LPS and declined with $MgSO_4$ and/or BMZ treatment. With LPS, principle cytokines/chemokine genes Interleukin1 beta (Il1b) (FIG. 6), [29], Tumor necrosis factor-alpha (Tnfa) (FIG. 7), [30], and C—C motif chemokine receptor 2 (Ccr2) (FIG. 8) [31], were significantly higher vs. PBS controls. Genes related to immune regulation and oxidative stress, Inhibitor of kappaB kinase beta (Ikbkb) [32] (FIG. 9) and Nitric Oxide Synthase 2 (Nos 2 aka iNOS) (FIG. 10) [33], were also significantly elevated with LPS vs. PBS. Evaluation of embryonic brains exposed to LPS and interventions, did result in lower expression of some but not all genes. For Il1b, only LPS exposed mice that received the combination of $MgSO_4$ and BMZ (LPS+$MgSO_4$/BMZ) showed lower expression vs. LPS alone. Tnfa was higher with LPS irrespective of the additional treatments. For the remaining genes, Ccr2, Ikbkb, and Nos2, LPS+$MgSO_4$/BMZ and LPS+TMPA were significantly lower vs. LPS. In contrast, expression in LPS+$MgSO_4$ or LPS+BMZ were only significantly lower for Ikbkb.

Figure 11:
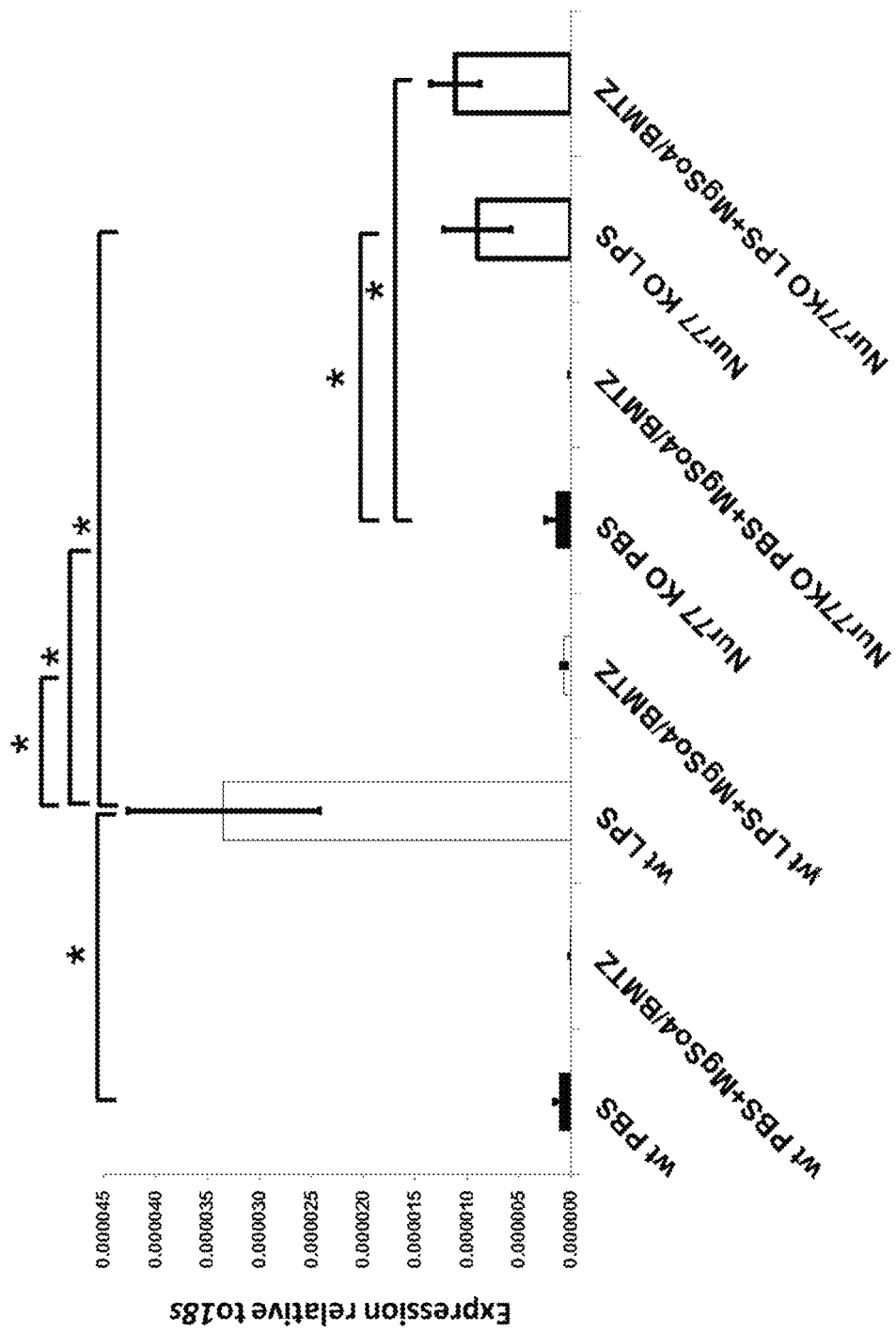
FIG. 11 is a graph showing the gene expression analysis of inflammatory marker Il1β comparing wildtype (wt) and Nur77 KO brains that were given control PBS and the injury LPS. There is an increase of Il1β in the Nur77 KO mice that was significantly lower when compared to the wt mice. With the addition of $MgSO_4$/BTMZ treatment, the wt inflammatory response was significantly lower than with LPS alone. In contrast, the Nur77 KO mice showed no difference with the addition of $MgSO_4$/BTMZ treatment or the vehicle control. * represent $P<0.05$ by students t-test. Error bars=SEM. BTMZ=betamethasone.
Figure 12:
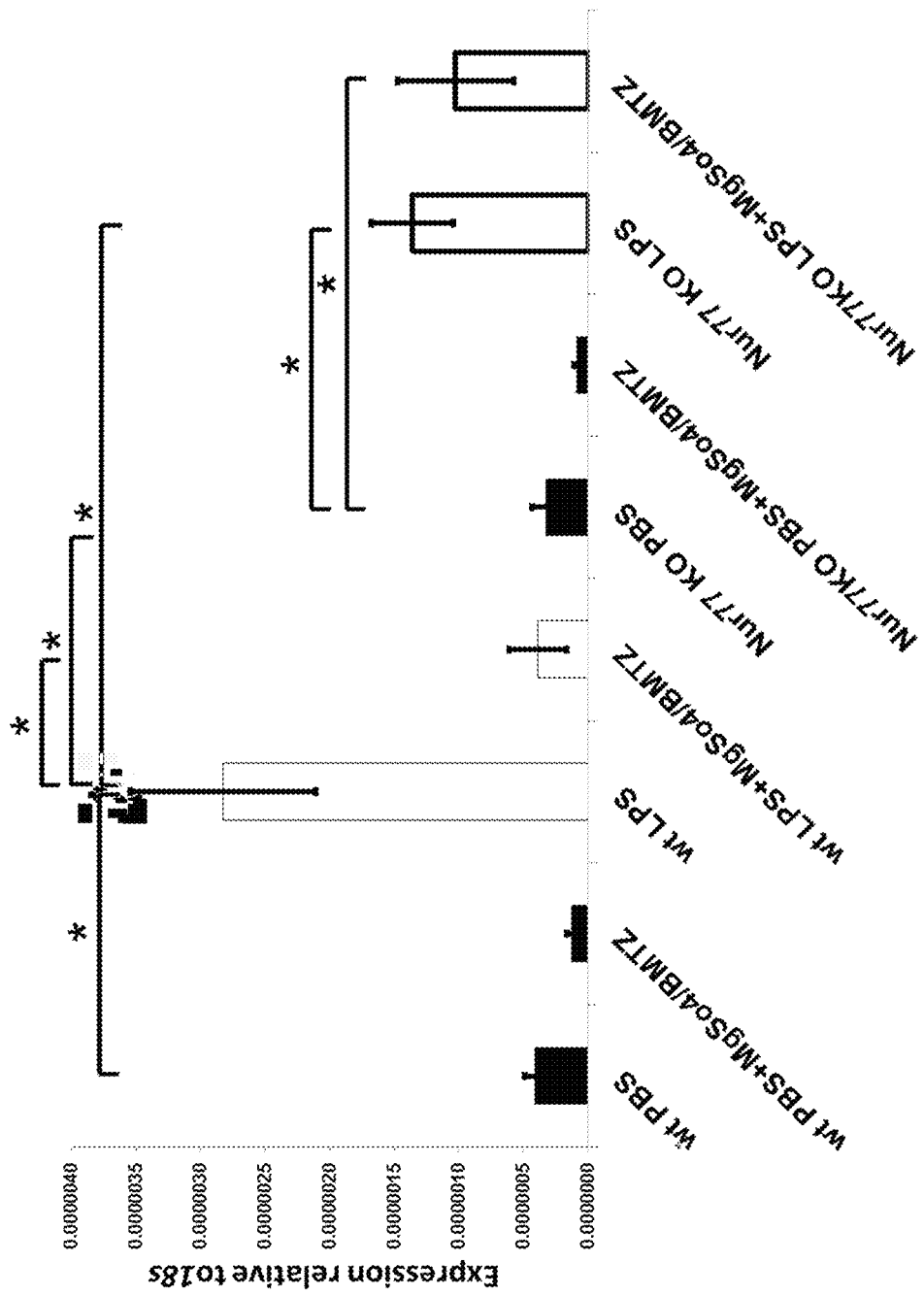
FIG. 12 is a graph showing the gene expression analysis of inflammatory marker IL6 comparing wildtype (wt) and Nur77 KO brains that were given control PBS and the injury LPS. There is an increase of IL6 in the Nur77 KO mice that was significantly lower when compared to the wt mice. With the addition of $MgSO_4$/BTMZ treatment, the wt inflammatory response was significantly lower than with LPS alone. In contrast, the Nur77 KO mice showed no difference with the addition of $MgSO_4$/BTMZ treatment or the vehicle control. * represent $P<0.05$ by students t-test. Error bars=SEM. BTMZ=betamethasone.

An increase in Il1β and IL6 was observed in WT brains of pups that were given LPS. In the Nur77 KO mice, an increase of Il1β and IL6 was observed, but it was significantly lower when compared to the WT mice. With the addition of $MgSO_4$/BTMZ treatment, the WT inflammatory response was significantly lower than with LPS alone. In contrast, the Nur77 KO mice showed no difference with the addition of $MgSO_4$/BTMZ treatment or the vehicle control. See FIG. 11 and FIG. 12.

REFERENCES

The following references are herein incorporated by reference in their entirety:

[1] BURDET J, RUBIO A P, SALAZAR A I, RIBEIRO M L, IBARRA C, FRANCHI A M. Inflammation, infection and preterm birth. Current pharmaceutical design 2014; 20:4741-8.
[2] In: Behrman R E, Butler A S, eds. Preterm Birth: Causes, Consequences, and Prevention. Washington (DC), 2007.
[3] LORENZ J M, WOOLIEVER D E, JETTON J R, PANETH N. A quantitative review of mortality and developmental disability in extremely premature newborns. Archives of pediatrics & adolescent medicine 1998; 152:425-35.
[4] CENTERS FOR DISEASE C, PREVENTION. Economic costs associated with mental retardation, cerebral palsy, hearing loss, and vision impairment—United States, 2003. MMWR Morbidity and mortality weekly report 2004; 53:57-9.
[5] AMERICAN COLLEGE OF 0, GYNECOLOGISTS' COMMITTEE ON PRACTICE B-O. Practice Bulletin No. 171: Management of Preterm Labor. Obstetrics and gynecology 2016; 128:e155-64.
[6] KENT A, LOMAS F, HURRION E, DAHLSTROM J E. Antenatal steroids may reduce adverse neurological outcome following chorioamnionitis: neurodevelopmental outcome and chorioamnionitis in premature infants. Journal of paediatrics and child health 2005; 41:186-90.
[7] RHEN T, CIDLOWSKI J A. Antiinflammatory action of glucocorticoids—new mechanisms for old drugs. The New England journal of medicine 2005; 353:1711-23.
[8] CAHILL A G, STOUT M J, CAUGHEY A B. Intrapartum magnesium for prevention of cerebral palsy: continuing controversy? Current opinion in obstetrics & gynecology 2010; 22:122-7.
[9] COSTANTINE M M, WEINER S J, EUNICE KENNEDY SHRIVER NATIONAL INSTITUTE OF CHILD H, HUMAN DEVELOPMENT MATERNAL-FETAL MEDICINE UNITS N. Effects of antenatal exposure to magnesium sulfate on neuroprotection and mortality in preterm infants: a meta-analysis. Obstetrics and gynecology 2009; 114:354-64.
[10] MITTENDORF R, DAMBROSIA J, PRYDE P G, et al. Association between the use of antenatal magnesium sulfate in preterm labor and adverse health outcomes in infants. American journal of obstetrics and gynecology 2002; 186:1111-8.
[11] ELOVITZ M A, BROWN A G, BREEN K, ANTON L, MAUBERT M, BURD I. Intrauterine inflammation, insufficient to induce parturition, still evokes fetal and neonatal brain injury. International journal of developmental neuroscience: the official journal of the International Society for Developmental Neuroscience 2011; 29:663-71.
[12] ELOVITZ M A, WANG Z, CHIEN E K, RYCHLIK D F, PHILLIPPE M. A new model for inflammation-induced preterm birth: the role of platelet-activating factor and Toll-like receptor-4. The American journal of pathology 2003; 163:2103-11.
[13] EKLIND S, HAGBERG H, WANG X, et al. Effect of lipopolysaccharide on global gene expression in the immature rat brain. Pediatric research 2006; 60:161-8.
[14] BONTA P I, MATLUNG H L, VOS M, et al. Nuclear receptor Nur77 inhibits vascular outward remodelling and reduces macrophage accumulation and matrix metalloproteinase levels. Cardiovascular research 2010; 87:561-8.
[15] HANNA R N, SHAKED I, HUBBELING H G, et al. NR4A1 (Nur77) deletion polarizes macrophages toward an inflammatory phenotype and increases atherosclerosis. Circulation research 2012; 110:416-27.
[16] KIM S O, ONO K, TOBIAS P S, HAN J. Orphan nuclear receptor Nur77 is involved in caspase-independent macrophage cell death. The Journal of experimental medicine 2003; 197:1441-52.
[17] ZHAO Y, HOWATT D A, GIZARD F, et al. Deficiency of the NR4A orphan nuclear receptor NOR1 decreases monocyte adhesion and atherosclerosis. Circulation research 2010; 107:501-11.
[18] LI L, LIU Y, CHEN H Z, et al. Impeding the interaction between Nur77 and p38 reduces LPS-induced inflammation. Nature chemical biology 2015; 11:339-46.
[19] HAMERS A A, ULEMAN S, VAN TIEL C M, et al. Limited role of nuclear receptor Nur77 in *Escherichia coli*-induced peritonitis. Infection and immunity 2014; 82:253-64.
[20] PEI L, CASTRILLO A, CHEN M, HOFFMANN A, TONTONOZ P. Induction of NR4A orphan nuclear receptor expression in macrophages in response to inflammatory stimuli. The Journal of biological chemistry 2005; 280:29256-62.

[21] CALNAN B J, SZYCHOWSKI S, CHAN FK, CADO D, WINOTO A. A role for the orphan steroid receptor Nur77 in apoptosis accompanying antigen-induced negative selection. Immunity 1995; 3:273-82.

[22] DAI Y, ZHANG W, SUN Q, et al. Nuclear receptor Nur77 promotes cerebral cell apoptosis and induces early brain injury after experimental subarachnoid hemorrhage in rats. Journal of neuroscience research 2014; 92:1110-21.

[23] DAI Y, SUN Q, ZHANG X, HU Y, ZHOU M, SHI J. Cyclosporin A ameliorates early brain injury after subarachnoid hemorrhage through inhibition of a Nur77 dependent apoptosis pathway. Brain research 2014; 1556: 67-76.

[24] DAI Y, ZHANG W, ZHOU X, SHI J. Inhibition of c-Jun N-terminal kinase ameliorates early brain injury after subarachnoid hemorrhage through inhibition of a Nur77 dependent apoptosis pathway. Neurochemical research 2014; 39:1603-11.

[25] ZHAN Y Y, CHEN Y, ZHANG Q, et al. The orphan nuclear receptor Nur77 regulates LKB1 localization and activates AMPK. Nature chemical biology 2012; 8:897-904.

[26] CHAO L C, WROBLEWSKI K, ZHANG Z, et al. Insulin resistance and altered systemic glucose metabolism in mice lacking Nur77. Diabetes 2009; 58:2788-96.

[27] HALLAK M, HOTRA J W, KUPSKY W J. Magnesium sulfate protection of fetal rat brain from severe maternal hypoxia. Obstetrics and gynecology 2000; 96:124-8.

[28] DOYLE A, MCGARRY M P, LEE N A, LEE J J. The construction of transgenic and gene knockout/knockin mouse models of human disease. Transgenic research 2012; 21:327-49.

[29] LEITNER K, A L SHAMMARY M, MCLANE M, JOHNSTON M V, ELOVITZ M A, BURD I. IL-1 receptor blockade prevents fetal cortical brain injury but not preterm birth in a mouse model of inflammation-induced preterm birth and perinatal brain injury. American journal of reproductive immunology 2014; 71:418-26.

[30] BURD I, BENTZ A I, CHAI J, et al. Inflammation-induced preterm birth alters neuronal morphology in the mouse fetal brain. Journal of neuroscience research 2010; 88:1872-81.

[31] PAINTLIA M K, PAINTLIA A S, SINGH A K, SINGH I. Attenuation of lipopolysaccharide-induced inflammatory response and phospholipids metabolism at the feto-maternal interface by N-acetyl cysteine. Pediatric research 2008; 64:334-9.

[32] MADSEN-BOUTERSE S A, ROMERO R, TARCA A L, et al. The transcriptome of the fetal inflammatory response syndrome. American journal of reproductive immunology 2010; 63:73-92.

[33] DONG Y, YU Z, SUN Y, et al. Chronic fetal hypoxia produces selective brain injury associated with altered nitric oxide synthases. American journal of obstetrics and gynecology 2011; 204:254 e16-28.

[34] WATTS JK, COREY D R. Silencing disease genes in the laboratory and the clinic. The Journal of pathology 2012; 226:365-79.

[35] HALLAK M. Effect of parenteral magnesium sulfate administration on excitatory amino acid receptors in the rat brain. Magnes Res. 1998; 11(2): 117-31. PMID: 9675756.

All scientific and technical terms used in this application have meanings commonly used in the art unless otherwise specified.

As used herein, the terms "subject", "patient", and "individual" are used interchangeably to refer to humans and non-human animals. The term "non-human animal" includes all vertebrates, e.g., mammals and non-mammals, such as non-human primates, horses, sheep, dogs, cows, pigs, chickens, and other veterinary subjects and test animals. In some embodiments of the present invention, the subject is a mammal. In some embodiments of the present invention, the subject is a human.

The term "salt" or "pharmaceutically acceptable salt" refers to salts and esters which are, within the scope of sound medical judgment, suitable for use in contact with the tissues of humans and lower animals without undue toxicity, irritation, and allergic response, commensurate with a reasonable benefit to risk ratio, and effective for their intended use. Representative acid additions salts include the hydrochloride, hydrobromide, sulphate, bisulphate, acetate, oxalate, valerate, oleate, palmitate, stearate, laurate, borate, benzoate, lactate, phosphate, tosylate, mesylate, citrate, maleate, fumarate, succinate, tartrate, ascorbate, glucoheptonate, lactobionate, and lauryl sulphate salts. Representative alkali or alkaline earth metal salts include the sodium, calcium, potassium, and magnesium salts.

As used herein, the terms "protein", "polypeptide" and "peptide" are used interchangeably to refer to two or more amino acids linked together. Groups or strings of amino acid abbreviations are used to represent peptides. Except when specifically indicated, peptides are indicated with the N-terminus on the left and the sequence is written from the N-terminus to the C-terminus. As used herein, the term "peptidomimetic", refers to molecules which are not polypeptides, but which mimic aspects of their structures. Peptidomimetic antagonists can be prepared by conventional chemical methods (see, e.g., Damewood J. R. "Peptide Mimetic Design with the Aid of Computational Chemistry" in Reviews in Computational Biology, 2007, Vol. 9, pp. 1-80, John Wiley and Sons, Inc., New York, 1996; Kazmierski W. K., "Methods of Molecular Medicine: Peptidomimetic Protocols," Humana Press, New Jersey, 1999).

As used herein, "antibody" refers to naturally occurring and synthetic immunoglobulin molecules and immunologically active portions thereof (i.e., molecules that contain an antigen binding site that specifically bind the molecule to which antibody is directed against). As such, the term antibody encompasses not only whole antibody molecules, but also antibody multimers and antibody fragments as well as variants (including derivatives) of antibodies, antibody multimers and antibody fragments. Examples of molecules which are described by the term "antibody" herein include: single chain Fvs (scFvs), Fab fragments, Fab' fragments, F(ab')2, disulfide linked Fvs (sdFvs), Fvs, and fragments comprising or alternatively consisting of, either a VL or a VH domain.

In some embodiments, the antibodies are monoclonal antibodies. In some embodiments, the monoclonal antibodies are obtained from rabbit-based hybridomas. As used herein, a compound (e.g., receptor or antibody) "specifically binds" a given target (e.g., ligand or epitope) if it reacts or associates more frequently, more rapidly, with greater duration, and/or with greater binding affinity with the given target than it does with a given alternative, and/or indiscriminate binding that gives rise to non-specific binding and/or background binding. As used herein, "non-specific binding" and "background binding" refer to an interaction that is not dependent on the presence of a specific structure (e.g., a given epitope). As used herein, an "epitope" is the part of a molecule that is recognized by an antibody.

As used herein, "binding affinity" refers to the propensity of a compound to associate with (or alternatively dissociate from) a given target and may be expressed in terms of its dissociation constant, Kd. In some embodiments, an antibody according to the present invention has a Kd of $10^{-5}$ or less, 10' or less, preferably 10' or less, more preferably $10^{-8}$ or less, even more preferably $10^{-9}$ or less, and most preferably $10^{-10}$ or less. Binding affinity can be determined using methods in the art, such as equilibrium dialysis, equilibrium binding, gel filtration, immunoassays, surface plasmon resonance, and spectroscopy using experimental conditions that exemplify the conditions under which the compound and the given target may come into contact and/or interact. Dissociation constants may be used determine the binding affinity of a compound for a given target relative to a specified alternative. Alternatively, methods in the art, e.g., immunoassays, in vivo or in vitro assays for functional activity, etc., may be used to determine the binding affinity of the compound for the given target relative to the specified alternative. Thus, in some embodiments, the binding affinity of the antibody for the given target is at least 1-fold or more, preferably at least 5-fold or more, more preferably at least 10-fold or more, and most preferably at least 100-fold or more than its binding affinity for the specified alternative.

The use of the singular can include the plural unless specifically stated otherwise. As used in the specification and the appended claims, the singular forms "a", "an", and "the" can include plural referents unless the context clearly dictates otherwise. As used herein, "and/or" means "and" or "or". For example, "A and/or B" means "A, B, or both A and B" and "A, B, C, and/or D" means "A, B, C, D, or a combination thereof" and said "combination thereof" means any subset of A, B, C, and D, for example, a single member subset (e.g., A or B or C or D), a two-member subset (e.g., A and B; A and C; etc.), or a three-member subset (e.g., A, B, and C; or A, B, and D; etc.), or all four members (e.g., A, B, C, and D).

The phrase "comprises, consists essentially of", or consists of is used as a tool to avoid excess page and translation fees and means that in some embodiments the given thing at issue comprises something, and in some embodiments the given thing at issue consists of something. For example, the sentence "In some embodiments, the composition comprises, consists essentially of, or consists of A" is to be interpreted as if written as the following two separate sentences: "In some embodiments, the composition comprises A. In some embodiments, the composition consists essentially of A. In some embodiments, the composition consists of A." Similarly, a sentence reciting a string of alternates is to be interpreted as if a string of sentences were provided such that each given alternate was provided in a sentence by itself. For example, the sentence "In some embodiments, the composition comprises A, B, or C" is to be interpreted as if written as the following three separate sentences: "In some embodiments, the composition comprises A. In some embodiments, the composition comprises B. In some embodiments, the composition comprises C."

Throughout the instant specification, drawings, and claims, a feature of an inventive embodiment may be discussed alone or in specific combination with another feature. The discussion of a given feature by itself or as a specific combination of features is not to be construed as limiting. Instead, embodiments of the present invention having the given feature alone and in combination with one or more other features are contemplated herein as if explicitly recited herein to the extent possible, e.g., except where the features are mutually exclusive, the given feature cannot be combined with the other feature, etc. For example, where Embodiment A discusses the presence of Feature 1, Embodiment B discusses Features 2 and 3, but no embodiment explicitly sets forth the combination of Features 1, 2, and 3, an embodiment comprising the combination of Features 1, 2, and 3 is contemplated herein as though the specific combination was explicitly recited so long as Features 1, 2, and 3 are combinable.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein but is only limited by the following claims.

What is claimed is:

1. A method of treating or inhibiting preterm birth of a fetus caused by abnormal expression of Nur77, which comprises administering to the fetus an effective amount of one or more Nur77 antagonists.

2. A method of treating or inhibiting a disease or disorder selected from preterm labor, preterm birth, perinatal neuroinflammation, a perinatal neurological injury, a vascular injury, a neurodevelopmental disability, and cerebral palsy in a subject in need thereof, which comprises reducing or inhibiting expression of Nur77 or reducing or inhibiting Nur77 receptor signaling in the subject by administering to the subject an effective amount of one or more Nur77 antagonists, wherein the disease or disorder is caused by abnormal expression of Nur77.

3. The method of claim 2, wherein the one or more Nur77 antagonists is a nucleic acid molecule, a protein, a peptidomimetic, an antibody or an antigen-binding fragment (Fab) thereof, a ribozyme, or a small molecule.

4. The method of claim 2, wherein the one or more Nur77 antagonists is ethyl 2-(2,3,4-trimethoxy-6-octanoylphenyl)acetate (TMPA) or a pharmaceutically acceptable salt thereof.

5. The method of claim 2, wherein a therapeutically effective amount of the one or more Nur77 antagonists is administered to the subject.

6. The method of claim 2, wherein a prophylactically effective amount of the one or more Nur77 antagonists is administered to the subject.

7. The method of claim 2, wherein a dose of the one or more Nur77 antagonists is administered before, during, and/or after preterm birth of the subject.

8. The method of claim 2, wherein the subject is a fetus or a premature baby.

9. The method of claim 8, wherein the fetus is treated in utero by administering the one or more Nur77 antagonists to the mother.

10. The method according to claim 1, wherein the one or more Nur77 antagonists are administered to the subject in an amount of about 5 mg to about 500 mg per kg weight of the subject.

11. The method according to claim 1, wherein the one or more Nur77 antagonists are administered in the form of a pharmaceutical composition.

12. The method according to claim 1, which further comprises administering to the subject magnesium sulfate and/or betamethasone.

13. The method according to claim 1, which further comprises administering to the subject one or more supplementary agents.

14. The method according to claim 13, wherein the one or more supplementary agents is a corticosteroid, an immunosuppressant, an anti-inflammatory agent, an anti-ischemic agent, or a palliative agent.

15. The method of claim 1, wherein the one or more Nur77 antagonists is a nucleic acid molecule, a protein, a peptidomimetic, an antibody or an antigen-binding fragment (Fab) thereof, a ribozyme, or a small molecule.

16. The method of claim 1, wherein the one or more Nur77 antagonists is ethyl 2-(2,3,4-trimethoxy-6-octanoylphenyl)acetate (TMPA) or a pharmaceutically acceptable salt thereof.

17. The method of claim 1, wherein the fetus is treated in utero by administering the one or more Nur77 antagonists to the mother.

18. The method according to claim 2, wherein the one or more Nur77 antagonists are administered to the subject in an amount of about 5 mg to about 500 mg per kg weight of the subject.

19. The method according to claim 2, which further comprises administering to the subject magnesium sulfate and/or betamethasone.

20. The method according to claim 2, which further comprises administering to the subject one or more supplementary agents.

21. The method according to claim 20, wherein the one or more supplementary agents is a corticosteroid, an immunosuppressant, an anti-inflammatory agent, an anti-ischemic agent, or a palliative agent.

* * * * *